United States Patent [19]
Forehand et al.

[11] Patent Number: 6,089,740
[45] Date of Patent: Jul. 18, 2000

[54] MULTIPURPOSE DENTAL LAMP APPARATUS

[75] Inventors: Joseph Mark Forehand; Vernon Kim Kutsch, both of Albany, Oreg.; Bryan G. Moore, Carlsbad; Dale Alan Rorabaugh, Rancho Sante Fe, both of Calif.

[73] Assignee: Kreativ, Inc., San Diego, Calif.

[21] Appl. No.: 09/004,217

[22] Filed: Jan. 8, 1998

Related U.S. Application Data

[60] Provisional application No. 60/057,154, Aug. 28, 1997.

[51] Int. Cl.[7] .............................. A61B 1/06; A61C 1/00; A61C 3/00; F21V 5/00; G01J 1/00
[52] U.S. Cl. .......................... 362/573; 362/572; 362/574; 362/575; 313/634; 313/638; 313/643
[58] Field of Search .................................. 313/10, 13, 11, 313/22, 24–25, 35–36, 48–49, 634, 638–343; 362/583, 138, 572–73, 293, 804, 574, 575; 433/203.1, 215, 229, 228.1, 226; 315/326, 241 R

[56] References Cited

U.S. PATENT DOCUMENTS

| | | | |
|---|---|---|---|
| 3,995,934 | 12/1976 | Nath | 350/96 |
| 4,009,382 | 2/1977 | Nath | 240/12 P |
| 4,112,335 | 9/1978 | Gonser | 315/241 R |
| 4,171,572 | 10/1979 | Nash | 362/573 X |
| 4,229,658 | 10/1980 | Gonser | 315/326 X |
| 4,385,344 | 5/1983 | Gonser | 362/573 |
| 4,608,622 | 8/1986 | Gonser | 362/573 |
| 4,661,070 | 4/1987 | Friedman | 433/203.1 |
| 4,666,406 | 5/1987 | Kanca, III | 433/229 |
| 4,747,662 | 5/1988 | Fitz | 350/96.32 |
| 4,952,143 | 8/1990 | Becker | 433/32 |
| 5,003,434 | 3/1991 | Gonser et al. | 362/572 |
| 5,032,178 | 7/1991 | Cornell | 106/35 |
| 5,035,621 | 7/1991 | Gottschalk | 433/226 |
| 5,125,842 | 6/1992 | Hiltunen | 433/226 |
| 5,283,718 | 2/1994 | Stephenson et al. | 362/572 |
| 5,335,648 | 8/1994 | Kozawa et al. | 362/138 X |
| 5,530,632 | 6/1996 | Shikano et al. | 362/804 X |
| 5,613,752 | 3/1997 | Vezard | 362/293 X |
| 5,645,428 | 7/1997 | Yarborough | 433/215 |
| 5,664,863 | 9/1997 | Cassarly et al. | 362/583 |

OTHER PUBLICATIONS

New Developments in Resin Restorative Systems, Jada vol. 128, May 1997 pp. 573–581, Karl F. Leinfelder.
Physical Properties and Gap Formation of Light–Cured Composites with and without Soft–Start Polymerization, Jrnl of Dentistry vol. 23, Nos. 3–4, pp. 321–330, 1997 A. Mehl, R. Hickel, and K–H Kunzelmann (no month).
Laser Tooth Whitening, Dentistry Today, vol. 15, No. 8, Aug. 1996.
Advertisement Flyer, Quasarbrite Laser Whitening Gel, from Interdent, Inc. (no date).

*Primary Examiner*—Michael H. Day
*Assistant Examiner*—Mack Haynes
*Attorney, Agent, or Firm*—Lori M. Friedman

[57] ABSTRACT

Disclosed is a lamp apparatus designed for both bleaching teeth and curing dental restorative materials. Both bleaching and curing modes of operation may be used in at least three different power levels designated as boost, ramp, and normal. The lamp apparatus contains a incandescent xenon-halogen bulb and a dichroic reflector which focuses filtered visible light on the end of a flexible light guide which is part of a handpiece for directing the transmitted light by the light guide to a tooth being treated. The lamp apparatus employs a slave microprocessor in a control panel mountable at different positions on a housing for the xenon-halogen bulb and a master microprocessor within the housing which is detachably connected to the slave microprocessor.

47 Claims, 12 Drawing Sheets

OPTICAL SYSTEM

MULTIPURPOSE DENTAL LAMP APPARATUS

RELATED PATENT APPLICATION

This is a utility patent application based on a U.S. provisional patent application Ser. No. 60/057,154 filed Aug. 28, 1997 and entitled "Multipurpose Dental Light and Method for Use."

BACKGROUND OF THE INVENTION

1. Field of the Invention

This invention relates to a dental lamp apparatus used for curing light activated restorative dental materials and for bleaching to whiten teeth. This lamp apparatus provides visible light with a sufficient power density to either rapidly cure restorative material or rapidly bleach a tooth. The lamp apparatus may be switched between these two modes of operation as desired by the dentist. Each mode has a plurality of power levels, one being a ramp power level, particularly suited for curing, enabling the dentist to select a light power density which changes in a controlled fashion best suited for the type of restorative material being cured.

2. Background Discussion

In the current practice of dentistry, it is common to bond porcelain or acrylic laminates to teeth for restorative and cosmetic purposes. The popularity of this procedure is due to its ease, aesthetic appeal, and minimization of trauma to the patient. It is also common to use composite resins or white cosmetic fillings for restorative procedures.

The bleaching to whiten teeth is also a subject of much current interest in the dental community. Besides the pleasurable effects of white teeth, discoloration of non-vital teeth is often a consequence of endodontic treatment, or in traumatized teeth which have experienced a loss of pulpal vitality. Vital teeth may become stained due to tetracycline prescribed for the patient for various medical reasons. Other causes of stained teeth may be drinking water with a high mineral content. Coffee drinking and using tobacco products are also sources of stained teeth. This type of stain is not always removable by conventional prophylactic treatment.

Lamps and lasers have been used for both curing and bleaching. Lamps with a constant beam but low light power density take a relatively long time to cure restorative material, typically, in excess of about 40 seconds. Recently, flash lamps with a high power density have been proposed, but they are deficient because in curing restorative dental materials they are unable to deliver low power levels to produce a ramp profile or pattern which shall be discussed subsequently in greater detail. Such flash lamps must simulate a lower power using a pulse mode which may not have the same effect on the restorative dental materials. Moreover, such flash lamps present a hazard to the eye. Lasers, which are expensive, are deficient because they provide light essentially only at one wavelength. This is undesirable, because the light activated materials react most effectively with light over a selected wavelength band, usually from about 400 to 600 nanometers (nm). Moreover, the lasers cannot normally be used for both curing and bleaching. Because of the high light power density from the lasers, the time it takes to cure restorative material is relative short, usually less than about 10 seconds. But great care must be employed when using lasers because this high power density of light can cause severe injury if the beam of laser light accidentally, for example, strikes the eye even briefly.

Unlike the instant invention, high powered visual light sources (VLS) may use a mercury xenon plasma arc lamp. There are other light sources, such as flashes or strobes, that may be employed. Additionally, such a high-powered instrument can use a high voltage spike to initiate the arc and an expensive power supply. These arc lamps are hard to use as they are quite inefficient and expensive to operate. The bulbs and power supply are expensive. Some bulbs require a 15 minute warm-up period. Adding to the expense and inconvenience of these bulbs is their short life expectancy and deteriorating output.

An example of curing lamps used to cure certain composite materials applied is taught in U.S. Pat. No. 4,666,406 by Kanca, III. This device uses a fiber optic wand with a light transmitting fiber optic tip. This art is concerned with using solid fibers to transmit light to cure dental composite material. There is no mention of use of this device to facilitate tooth bleaching.

Optical fibers are again mentioned in, for example, U.S. Pat. No. 4,608,622 to Gosner. This art is again dealing with fiber light conducting bundles to transmit light to cure dental resin material as well as for oral illumination. Again, there is no mention of bleaching.

Curing lights with other ancillary features include U.S. Pat. No. 5,125,842 to Hiltunen. In this patent, monitoring the depth of cure is key, as is curing dental restorations.

U.S. Pat. No. 4,747,662 to Fitz discusses fiber optics with a liquid core and a fluoroplastic cladding. Fitz does not mention the light with relation to dental procedures.

Nath, in U.S. Pat. No. 3,995,934 also mentions a flexible light guide with a liquid center but does not mention dental use. Nath does mention the polymerization of dental resins in U.S. Pat. No. 4,009,382 in which a flexible light guide is described. There is, however, no mention of the light as a tool for bleaching, or whitening, of teeth.

There have also been various methods and systems available for tooth bleaching. Much of this technology, as evidenced by U.S. Pat. No. 5,645,428 to Yarborough, show that laser technology plays a large part in bleaching, or tooth whitening. Yarborough uses laser light to activate bleaching agents to accomplish tooth whitening. More specifically, an oxygen radical is activated by laser light.

A non-laser method for bleaching stained teeth by applying a concentrated solution of peroxide to stained teeth and focusing a beam of light at the teeth has been patented by Friedman in U.S. Pat. No. 4,661,070. The focused beam contains the combination of ultraviolet and infrared energy for activating the peroxide solution.

Another composition for bleaching teeth comprises aqueous hydrogen peroxide and a non-aqueous component which are combined to treat the teeth in response to the application of optical energy as disclosed by Cornell in U.S. Pat. No. 5,032,178. This patent teaches the use of chemical compositions, such as manganese sulfate and ferrous sulfate, to activate catalytically the bleaching activity of the light-activated hydrogen peroxide composition. The process of the instant invention uses no such materials.

The use of bleaching, as with peroxide, to whiten teeth appears less often in dental literature than laser whitening for use by dentists. Options such as at-home bleaching kits and whitening toothpastes are limited in their abilities and not comparable to laser bleaching or the professional dental bleaching results of this invention.

SUMMARY OF THE INVENTION

This invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide its benefits, which include (i) providing a light of sufficiently high power density to rapidly cure light activated dental restorative material or bleach teeth, (ii) versatility in that the lamp apparatus of this invention may be oriented in different positions or mounted to a vertical structure, (iii) enabling the dentist to recalibrate the light source.

The first feature of the lamp apparatus of this invention is that it includes a handpiece having a tip. The tip has an outlet of a diameter of from about 0.1 to about 20 millimeters through which an essentially continuous light beam emanates. In other words, the light from the tip is constant and non-intermittent.

The second feature is a light bulb positioned within a reflector which focuses light from the bulb at a predetermined point along an optical path. The bulb, when energized, for example, by a manually operated activation switch, emits light of sufficient intensity so that the light emanating from the tip has a power density of at least about 800 milliwatts per square centimeter, preferably from about 1000 to 2000 milliwatts per square centimeter. The bulb has an enclosure holding a mixture of xenon and halogen gases and employs a tungsten filament. At a predetermined applied voltage of about 24 volts the light emanating from the tip of the handpiece has a power of 250 watts or greater. The reflector has an ellipsoidal configuration with a longitudinal axis coincident with the optical path and a focal point along the optical path. The bulb has an elongated filament disposed axially along the reflector's longitudinal axis, and this filament, when the bulb is energized, has at one section thereof light which is brighter than at other sections of the filament. This brighter section is near or at the focal point. The reflector is of the dichroic type which passes infra red radiation through it.

The third feature is a filter along the optical path in advance of said predetermined point through which a predetermined wavelength of light in the visible range passes. In the preferred embodiment of this invention, there are a plurality of filters which are selectively moved into the optical path to vary the wavelength of light being transmitted to the tip of the handpiece. There is a first mode of operation for bleaching of teeth and a second mode of operation for curing of light activated dental restorative material. When in the first mode of operation for bleaching of teeth, the filtered light has a wavelength of from about 400 to about 550 nanometers. When in the second mode of operation for curing the dental restorative material, the filtered light has a wavelength from about 400 to about 500 nanometers. In each of mode of operation there are a plurality of power levels. These power levels include (a) a normal power level where the power density of the light emanating from the tip is substantially constant, (b) a ramp power level where the power density of the light emanating from the tip changes in a predetermined fashion, (c) a boost power level where the light emanating from the tip is from 15% to 25% greater than at the power density at the normal power level. At the normal power level the power density is from 800 to 1500 milliwatts per square centimeter. At the ramp power level there are a plurality of different patterns of power density which are selectable by the user.

The fourth feature is a flexible light guide between the handpiece and the predetermined point which transmits the light of said predetermined wavelength to the tip from which said light emanates. The light guide comprises a liquid enclosed in a flexible tubular member having an inside diameter ranging from about 2 to about 14 millimeters and a length from about 4 to about 10 feet. The tubular member is made from a material which is impermeable to the liquid and has a higher refractive index than the liquid. The liquid used to transmit the light in the light guide does not wet an internal surface of the light guide that it contacts, is not hygroscopic, has a refractive index lower than that of the material from which the tubular member is made.

The fifth feature is a control circuit including a detector which monitors the voltage applied to the bulb and a microprocessor electrically coupled to the detector and responsive thereto to adjust the voltage to maintain the desired power density of light emanating from said tip. a radiometer for reading the power density of the light emanating from the tip. There is a display for error or other messages and the microprocessor is programmed to include a routine for handing errors and providing messages for the display. There also is a signal device which alerts a user of the time elapsed while performing certain dental operations. Optionally, a light sensor detects light propagating along the optical path and provides a control signal used to regulate the voltage being applied to the bulb to maintain the power density of the bulb substantially constant. By substantially constant, it is meant that the power density may vary by as much as 15–20%.

The sixth feature is a housing enclosing the bulb and the reflector and a fan within the housing adjacent the bulb and reflector. The fan is operated to circulate air through the housing. There is a sensor which detects temperature within the housing and the fan is operated when the temperature exceeds a predetermined limit. The housing has a connector which enables it to be attached to a vertical structure. There is an opening in a wall of the housing at which the light is focused. The light guide is mounted on the exterior of the housing, and has one end detachably connected to the opening. A detector detects when the light guide has been detached and provides a control signal. The control circuit responds to this control signal to prevents the bulb from being energized or, if energized, deenergizes the bulb to discontinue light emission. On the exterior of the housing is a radiometer having a first operational mode for reading the power density of the light emanating from the tip, and a second operational mode for calibrating the bulb.

The seventh feature is a control panel on the housing which may be detached and attached to different locations. For example, the control panel may be at one or the other of two predetermined different locations on the housing, or attached to a remote location. The control panel includes a slave microprocessor and the housing includes a master microprocessor. The housing has a first cable for connecting the slave and master microprocessors together when the control panel is in the one location and a second cable for connecting the slave and master microprocessors together when the control panel is in the other location, thereby enabling the lamp apparatus to be disposed in different orientations. The control circuit is responsive to a control signal and deenergizes the light source to discontinue light emission whenever the control panel is detach and the light source is energized.

This invention also includes a number of methods. One method is for bleaching teeth, and it comprises (a) covering at least a portion of the surface of a tooth being treated with a bleaching agent, and (b) irradiating the bleaching agent with a beam of light from a xenon-halogen bulb filtered to provide light having a wavelength from 400 to 550 nanometers and a power density in excess of 1000 milliwatts per square centimeter for a sufficient time not to exceed one minute to bleach said tooth.

The bleaching agent may be concentrated hydrogen peroxide. In this method, preferably the steps of covering the tooth with the bleaching agent and then irradiating with light are repeated at least three times separately.

Another method is directed to restoration of a tooth, and it includes (a) covering at least a portion of the surface of a tooth being treated with light activated restorative dental material, and (b) irradiating the restorative dental material with a beam of light from a xenon-halogen bulb filtered to provide light having a wavelength from 400 to 500 nanometers and a power density of 1000 milliwatts per square centimeter or greater for a sufficient time to cure said material effectively.

The restorative dental material cures essentially completely within 15 seconds or less when said material has a thickness of 2 millimeters or less.

A third method is for treating a tooth with a light activated restorative material, including (a) providing a handpiece having a light outlet with a diameter of no greater than 20 millimeters from which emanates a continuous beam of light having a spectrum of from 420 to 580 nanometers and a power density of from 800 to 2000 milliwatts per square centimeter, and (b) while holding from the restorative material the tip of the handpiece a distance which no greater than 5 millimeters, directing said light beam on the restorative material for a time sufficient to effectively cure said material.

DESCRIPTION OF THE DRAWING

The preferred embodiment of this invention, illustrating all its features, will now be discussed in detail. This embodiment depicts the novel and non-obvious multipurpose dental lamp apparatus and method of this invention as shown in the accompanying drawing, which is for illustrative purposes only. This drawing includes the following figures (FIGS.), with like numerals indicating like parts.

DETAILED DESCRIPTION OF PREFERRED EMBODIMENT

Figure 1:
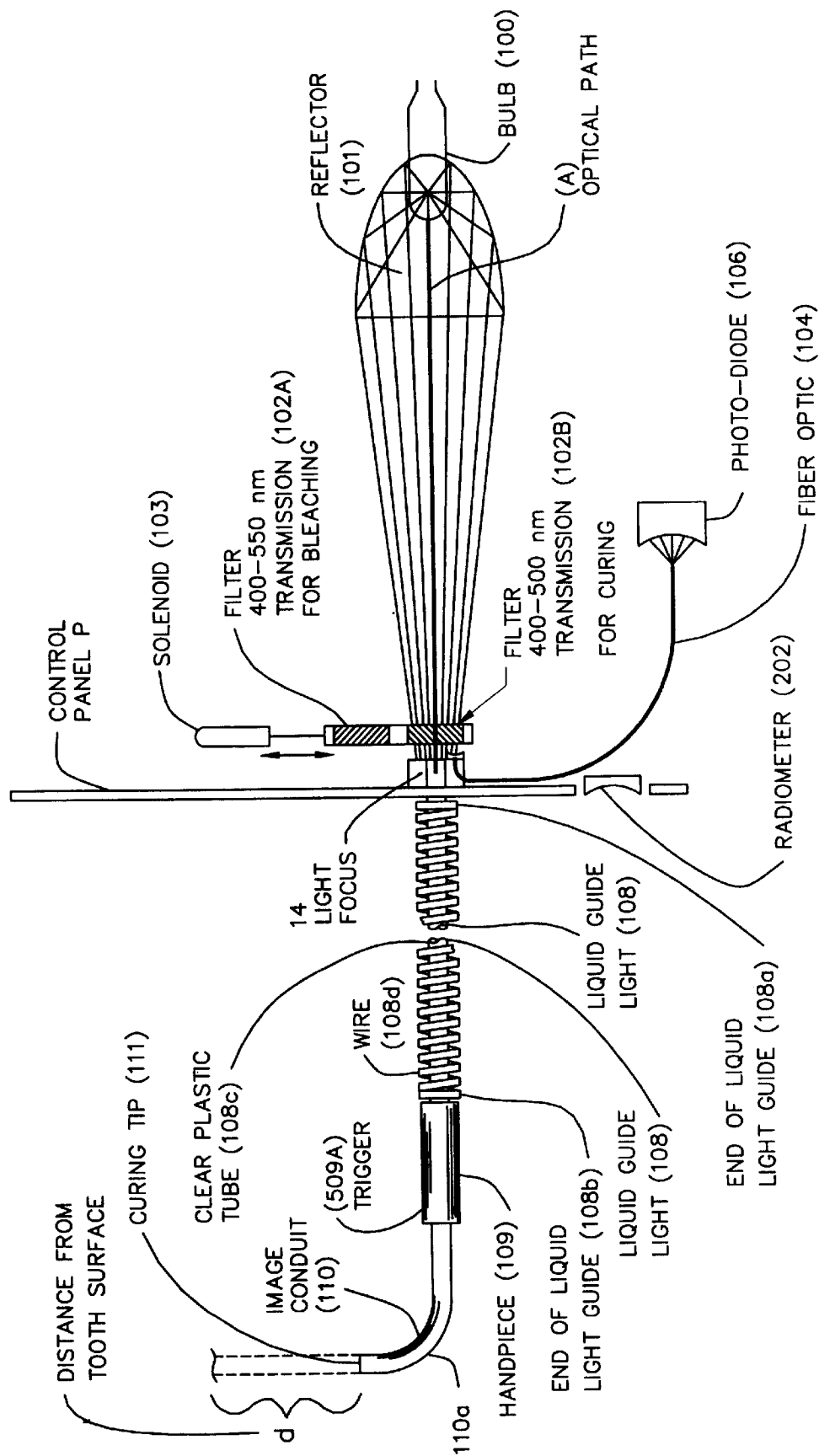
FIG. 1 is a schematic view of the dental lamp apparatus of the present invention.
Figure 2:
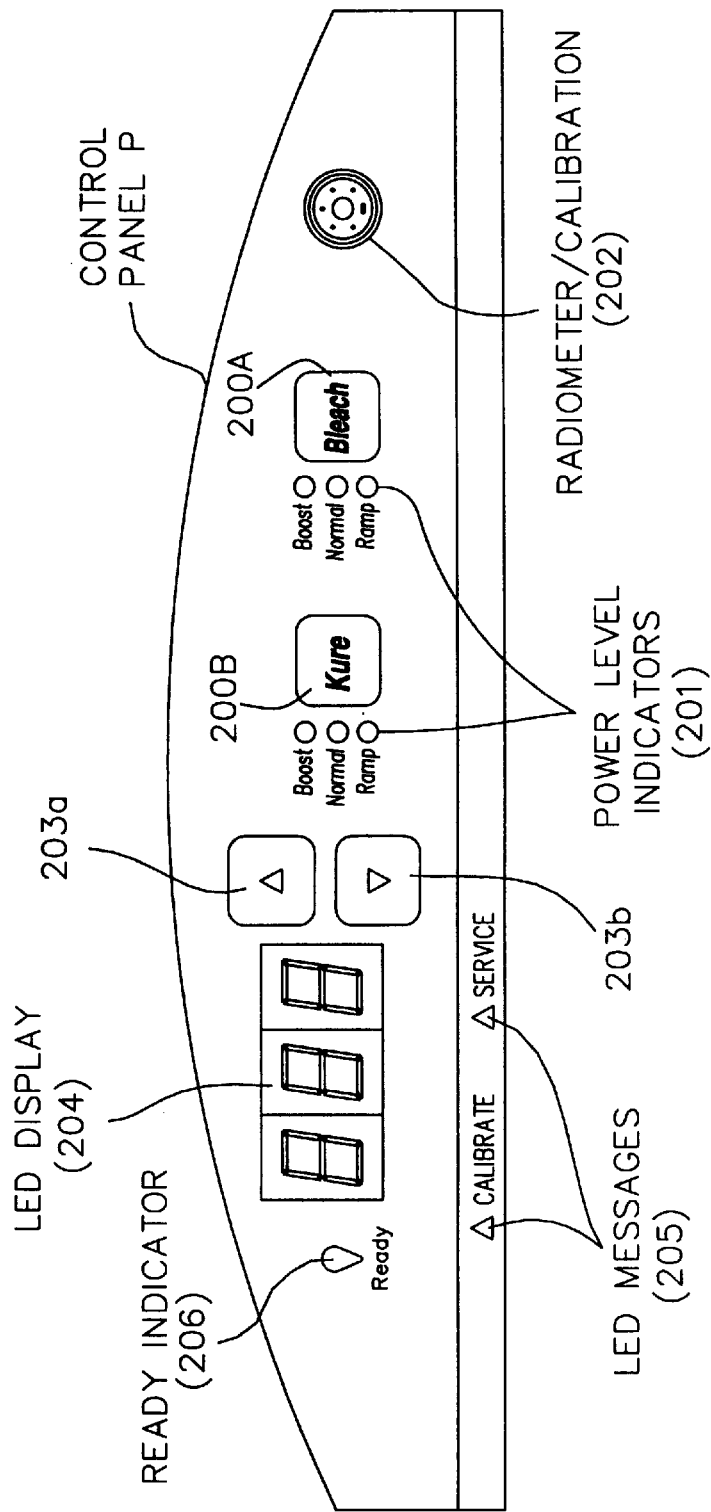
FIG. 2 depicts the control panel of the dental lamp apparatus.

As illustrated in FIGS. 1 and 2, the major components of the dental lamp apparatus 10 of this invention include a bulb 100, an ellipsoidal dichroic reflector 101 which partially surrounds the bulb 100, two filters 102A and 102B in the optical path A (FIG. 1) of the light from the bulb 100, a light guide 108 which collects the filtered light and forwards this light to a handpiece 109 used by the dentist to direct the filtered light against the surface of the tooth structure being treated. A suitable light guide 108 is sold by Fiber Optics Technology of Ponifret, Conn. under Part No. 210098-1. Connected to the handpiece 109 is an image conduit 110. The image conduit 110 is fiber bundle of approximately 1800 fibers which may be made of quartz or a similar light conducting material. Although there is some loss of energy, the multiplicity of fibers reduces the loss through the bend 110a and the image conduit 110 may be detached from the light guide 108 and sterilized in an autoclave, whereas the light guide would be damaged by autoclaving. The image conduit 110 carries light passing through the light guide 108 to a curing tip 111 at the distal end of the image conduit 110. The curing tip 111 is positioned by the dentist adjacent the tooth being treated a distance d a few millimeters (mm), about 1–5 mm from the tooth's surface to complete curing or bleaching procedures.

Figure 3:
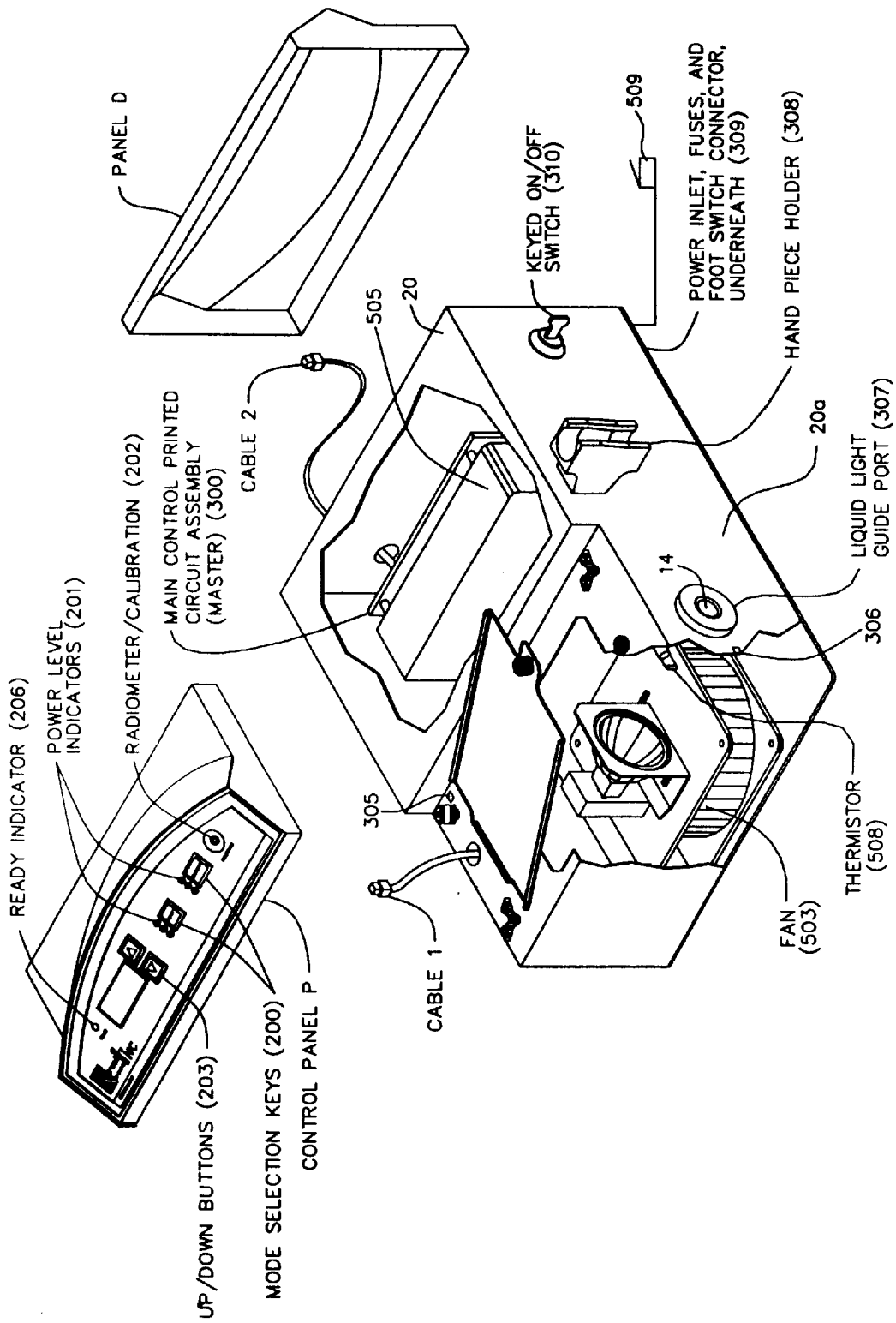
FIG. 3 is an exploded perspective view of the dental lamp apparatus of this invention.
Figure 5:
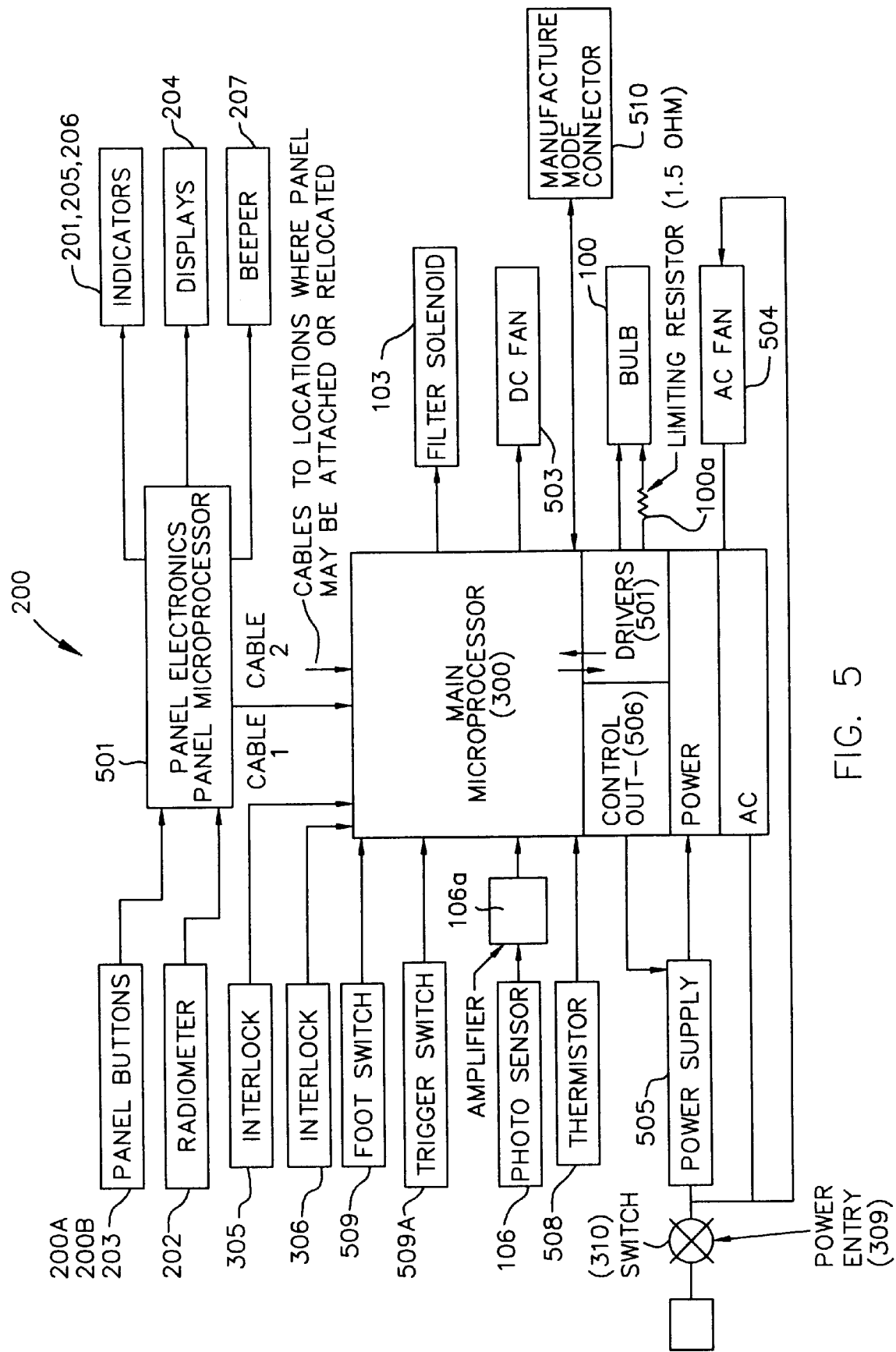
FIG. 5 is a circuit diagram of the electronic controls for the dental lamp apparatus of this invention.

The bulb 100, reflector 101, filters 102A and 102B are mounted within a box-like housing 20 and the light guide 108 with attached handpiece 109 extend from one side 20a of the housing 20. There is a holder 308 in which the handpiece 109 is seated when not being used. A fan 503 is positioned below the bulb 100 and reflector 101 and draws cool air into the housing 20 for cooling. Preferably, this fan 503 runs continuously while the bulb 100 is energized and for up to three (3) minutes after the bulb is deenergized. The fan 503 is turned on if the temperature inside the housing 20 rises to in excess of 50 degrees Centigrade. degrees Centigrade to dissipate heat from the power supply 505. A thermistor 508 in the housing 20 provides a signal to a master microprocessor 300 (FIG. 5) in a control circuit 200 for inhibiting the operations of the lamp apparatus 10 at excessively high temperatures. As shown in FIGS. 1, 3, and 5, the operation of the lamp apparatus 10 may be controlled alternately with either a trigger switch 509A or foot switch 509. The trigger switch 509A may be part of the dental handpiece 109.

As seen in FIGS. 2 and 3, the lamp apparatus 10 has a removable control panel P including a pair of buttons 200A and 200B used to select the lamp apparatus's operational mode. Pressing the button 200A selects the BLEACH mode and pressing the button 200B selects the KURE mode. As shown in FIG. 3, the dentist turns the lamp apparatus 10 on by turning the keyed ON/OFF switch 310 (FIG. 3). The dentist will then select the desired mode of operation by pressing either button 200A or 200B on the control panel P. These mode selection buttons 200A and 200B allow the dentist to either cure dental resins or bleach teeth by indicating the desired operation. Each of the operation selections has its own power level indicators 201. These power level indicators 201 are marked "boost," "normal," and "ramp," and are illuminated depending on the power level selected by the dentist. Both KURE and BLEACH modes each have these three power level selections available. If the button 200B is pressed while in the KURE mode, the power level is advanced from "normal" to "boost." These messages etc. are displayed in an LED display 204. If the button 200B is pressed again, the power level will advance from "boost" to "ramp." Likewise, if the button 200A is pressed while in the BLEACH mode, the power level is advanced from "normal" to "boost." If the button 200A is pressed again, the power level will advance from "boost" to "ramp."

There are LED messages 205 which are illuminated when the calibration is in progress. The display 204 flashes "CAL" shortly after the power up sequence of the program as discussed in greater detail subsequently if calibration is needed. Also, the lamp apparatus 10 is equipped with a ready light 206 which is illuminated when the lamp apparatus 10 is ready for operation.

There are up/down buttons 203a and 203b which allow the dentist to scroll through different "ramp" power level patterns or set calibration values at the factory during manufacture, as will be discussed subsequently. Initially the ramping power levels are the same for curing and bleaching, typically following a linear or exponential increase in power density over several seconds, in contrast with earlier instruments which change from one fixed level to another fixed level. New restorative materials or bleaching solutions as well as research into properties of existing materials are likely to reveal more ideal light energy versus time profiles. Therefore, the up and down buttons 203 may be used to select from a plurality of factory defined ramping power levels, with light energy versus time profiles being recalled from tables or algorithms (not shown) stored in the memory of the microprocessor 300. The up and down buttons 203 signal the microprocessor 300, though they do not change from the initial ramp immediately, in order to reduce the possibility of an accidental change, but act after a delay of two seconds. Thereafter, the display 204 indicates r##, where the ## is a numeric or character message identifying the internally programmed alternative ramp selected.

Another refinement is the possibility for a user to store their own "user-defined" ramp or ramps, indicated by a display of "rU#", where # represents a digit 0–9. The user presses the KURE or BLEACH button 200A or 200B quickly, and then the subsequent values corresponding to seconds or power density slope per minute may be selected by quickly pressing the up and down buttons. Pressing KURE or BLEACH quickly advances through each value in a given user-defined ramp, for example, number of seconds at initial power level, ramp slope to next power level, number of seconds at next power level, and so on. Pressing and holding the up or down buttons 203 cancels the user-defining operation and reverts to displaying the factory or user defined display "r##". Pressing KURE or BLEACH for two seconds saves the values into a register file 81 (FIG. 6) and the microprocessor 300 and transfers the values to an EEPROM 90 (FIG. 6) so they will remain valid even after interrupting and restoring lamp power.

As shown in FIG. 3, at the rear of the housing 20 is a second removable panel D. The control panel P is located on the top of the housing 20 and the rear panel D is located at the back of the housing 20. This allows the dentist to reconfigure the lamp apparatus 10 for horizontal or vertical orientation by exchanging panel positions putting the control panel P at the rear of the housing 20 and covering the top of the housing with the panel D. A main control panel printed circuit assembly 300a is disposed within the housing 20 and it includes the master microprocessor 300 which is connected to a slave microprocessor 501 in the control panel P. A serial communication cable (SCC) labeled as cable 1 connects the slave microprocessor 501 to the master microprocessor 300 when the control panel P is positioned on the top of the housing 20. Another serial communication cable (SCC) labelled as cable 2 located near the rear of the housing 20 connects the slave microprocessor 501 to the master microprocessor 300 when the control panel P is positioned at the rear of the housing 20. Either cable 1 or 2 is connected easily with a modular connector C which is attached at the end of each cable.

Figure 10:
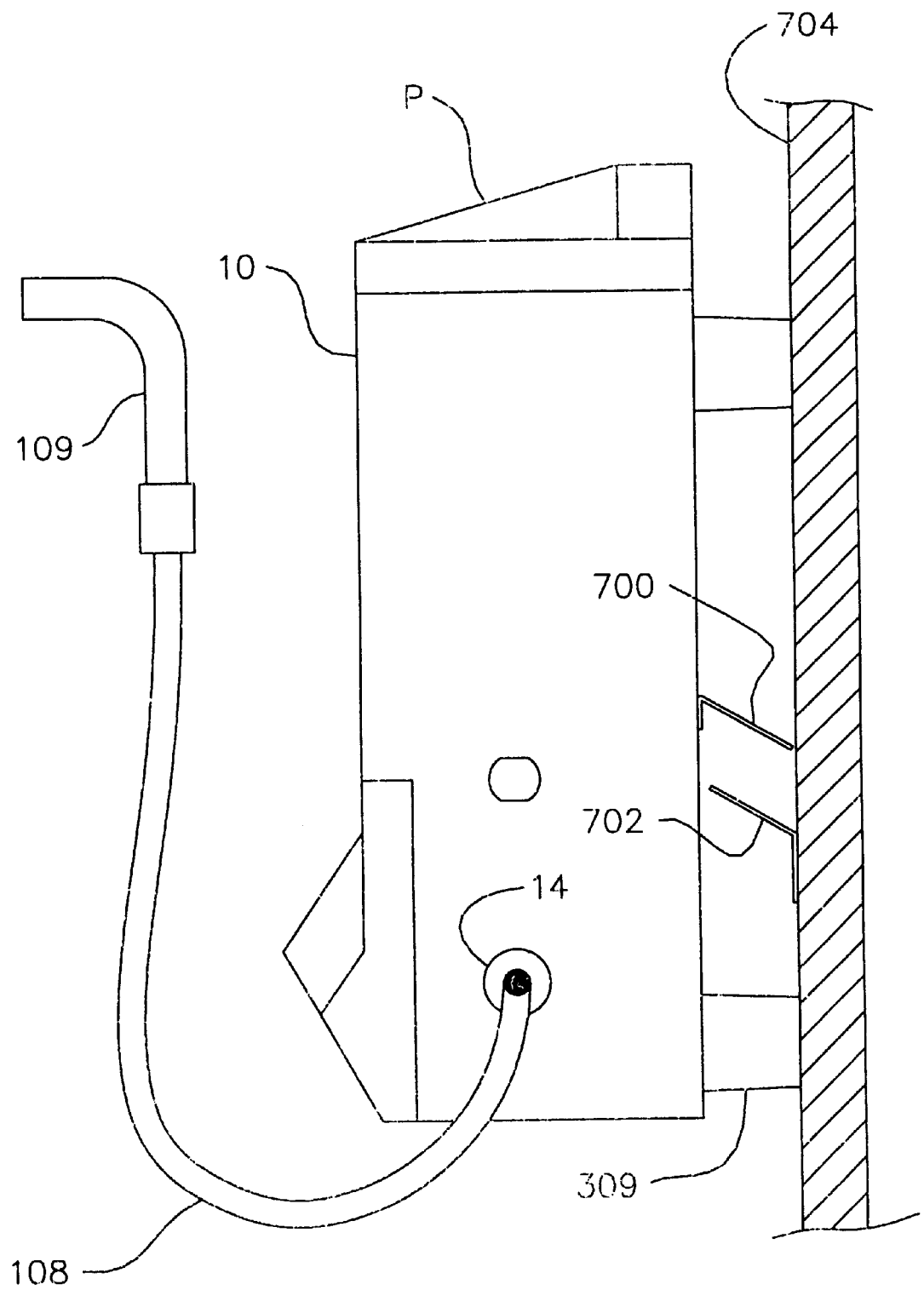
FIG. 10 is a schematic side elevational view, partially in cross-section, of the lamp apparatus of this invention mounted to a vertical structure.

For use in a horizontal, or counter top, orientation, the dentist will use cable 1 and position the control panel P on the top of the housing 20. If the dentist desires vertical, or wall mounted, orientation, the dentist will remove control panel P, disconnect cable 1 and then reposition the panel P at the rear of the housing and connect the cable 2 to the panel P and position the panel D on the top of the housing. As shown in FIG. 10, there is a connector 700 fixedly attached to the underside 309 of the housing 20 which is used to detachably connect the housing to a vertical wall structure 704 which has a mating connector 702 fixedly attached to the vertical wall structure.

There is an interlock switch 305 in the housing 20 near its top which detects when either panel P or D is on the top of the housing. The lamp apparatus 10 may be positioned on the countertop, on the dentist's air abrasion unit, or as a wall-mounted unit. The lamp apparatus 10 is thus designed for variable positioning and is portable, weighing less than 15 pounds. The lamp apparatus 10 can be easily carried from room to room. This leaves more free space in the dental operatory and allows easy portability and added accessibility.

Figure 1A:
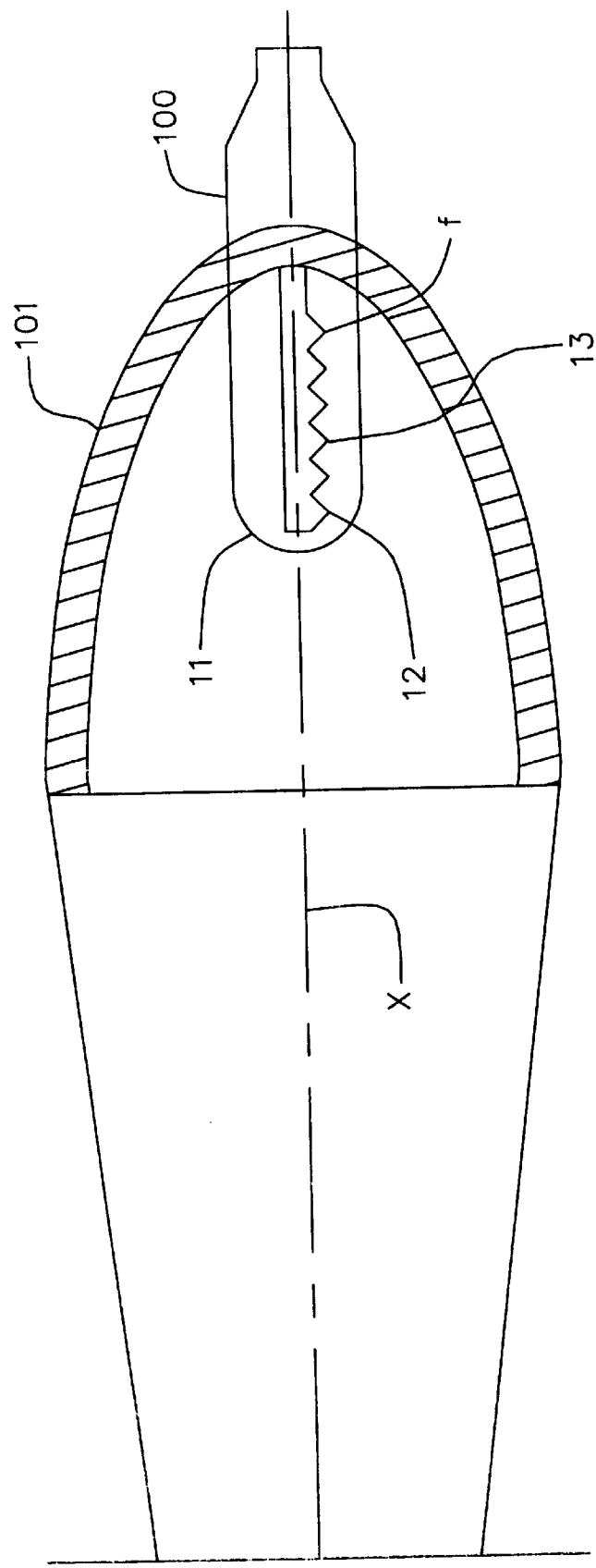
FIG. 1A is an enlarged, fragmentary, cross-sectional view of the bulb within the reflector.

As best shown in FIG. 1A, the bulb 100 has a glass enclosure 11 containing a mixture of xenon and halogen gases with a tungsten filament 12 having a major portion of this filament coincident with the longitudinal axis X (FIG. 1A) of the reflector 101. The optical path A is at least partially coincident with the longitudinal axis X of the reflector 101. When the bulb 100 is energized, this filament 12 has one section, a "hot spot" 13, at which the maximum brightness occurs which is substantially brighter than other sections of the filament. The bulb 100 preferably is positioned so that this hot spot 13 is coincident with the focal point f of the reflector 101.

Figure 8:
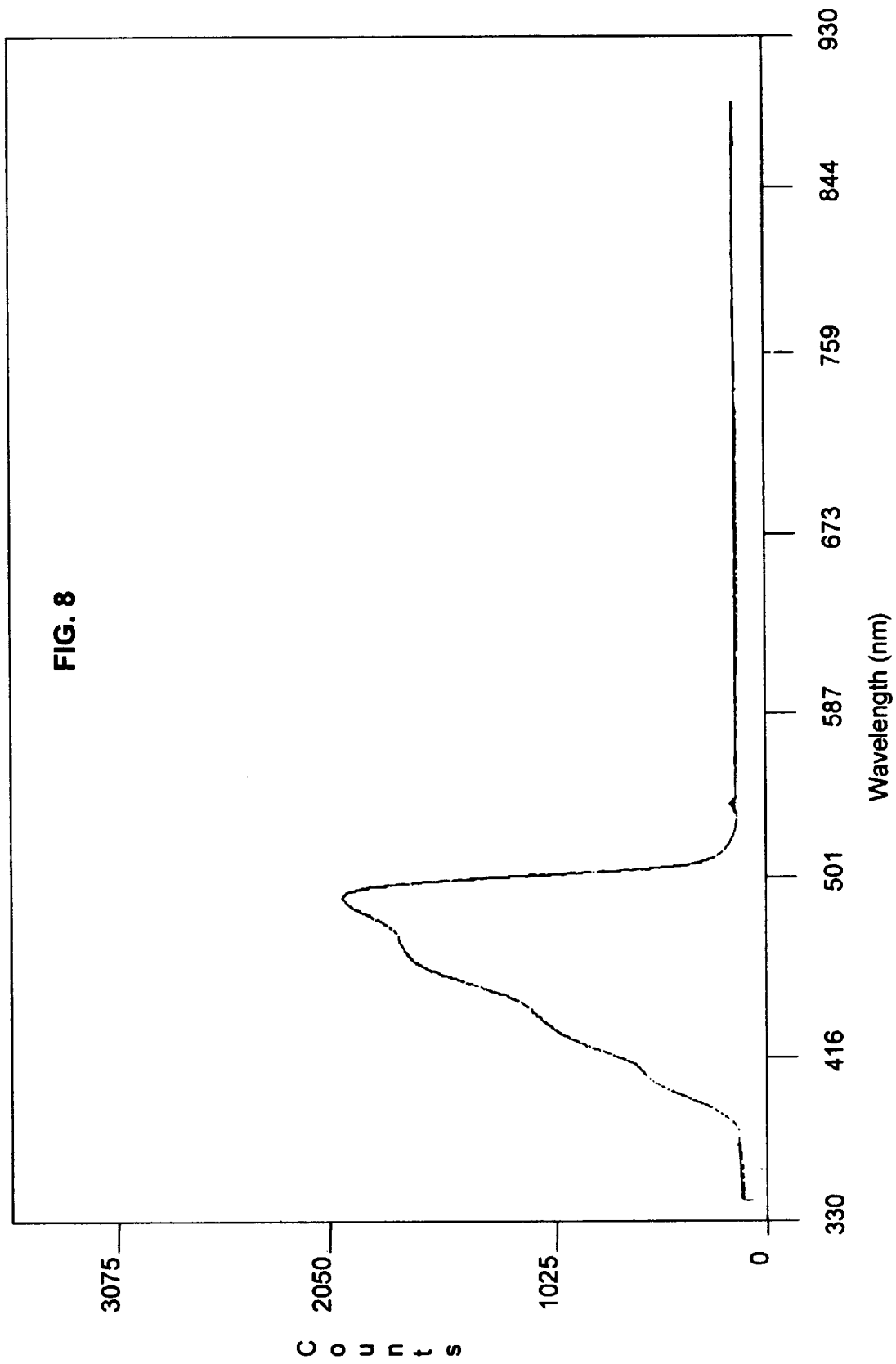
FIG. 8 is a graph illustrating the spectrum of the filtered blue light emanating from the tip of the handpiece used for curing.
Figure 9:
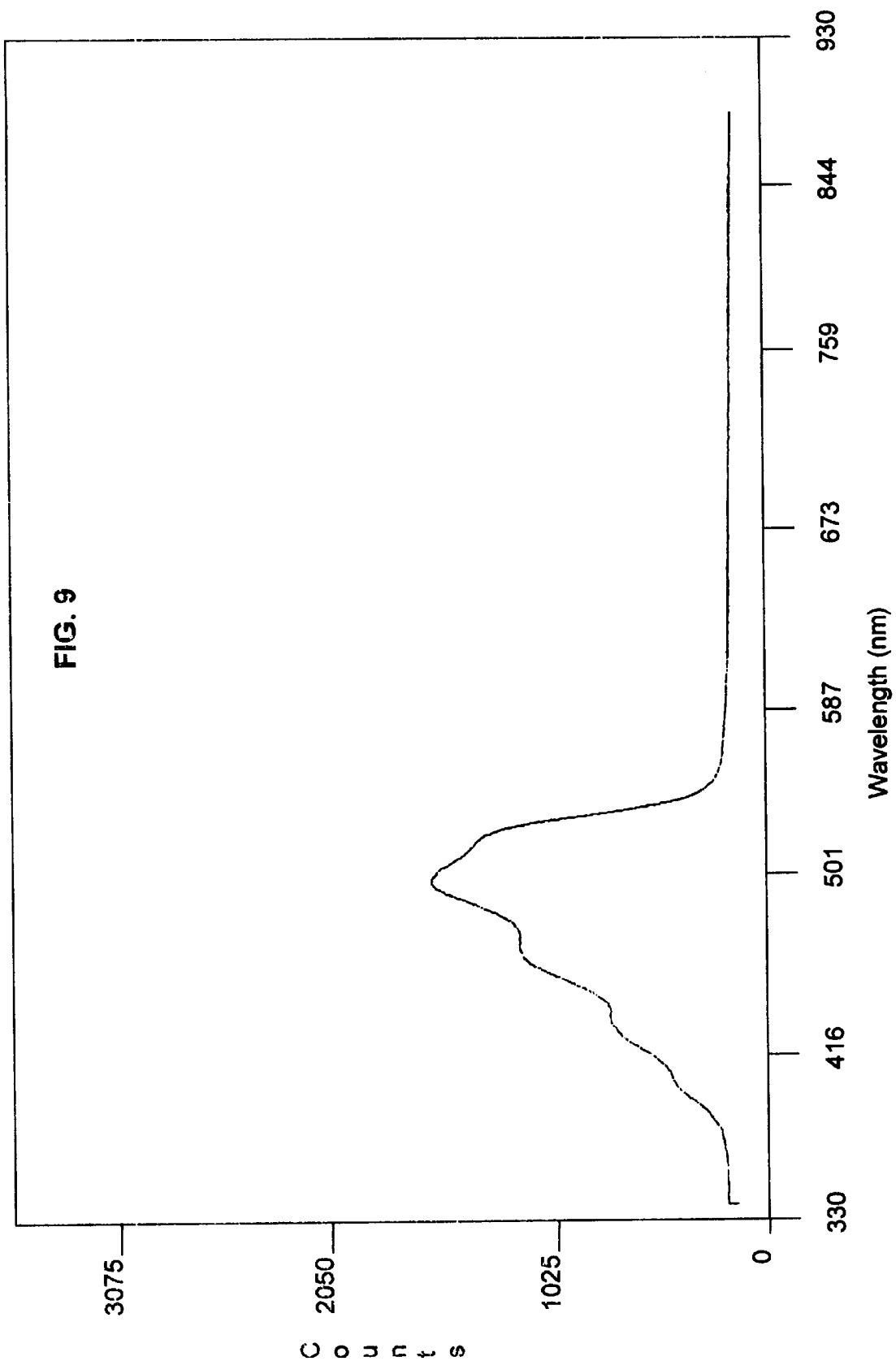
FIG. 9 is a graph illustrating the spectrum of the filtered green light emanating from the tip of the handpiece used for bleaching.

The bulb 100 is within the dichroic reflector 101 so that some of the light from the bulb 100 is reflected along the optical path A to intersect with one of the filters 102A or 102 B, depending on the condition of a solenoid 103 which moves these filters into position in the optical path A. The filter 102A is for bleaching and the light passing through this filter has a wavelength ranging from about 400 to about 550 nm. The filter 102B is for curing and the light passing through this filter has a wavelength from about 400 to about 500 nm. A typical spectrum of the blue light passing through the filter 102B and emanating from the tip 11 of the handpiece 109 is depicted in FIG. 8. A typical spectrum of the green light passing through the filter 102A and emanating from the tip 11 of the handpiece 109 is depicted in FIG. 9. The filters 102A and 102B are mounted on a spring loaded mechanism (not shown) so that when the solenoid 103 is deenergized, the cure filter 102B is positioned in the optical path A. When the solenoid 103 is energized, the bleaching filter 102A is moved into the optical path A.

The preferred reflector 101 is an MR 16, ellipsoidal reflector having a focal length of 32 mm with the focused reflected light at the focal point providing a "spot" with a diameter of about 10 mm. Its internal surface is coated with a dichroic material. The bulb 100 is filled a mixture of xenon and halogen gases and provides 250 watts of power with an applied voltage 24 volts. The ellipsoidal reflector 101 focuses the light at a predetermined "spot" or circular area 14 along the optical path which corresponds to an opening or light guide port 307 (FIG. 3) having a diameter of from about 2 to 14 millimeters depending on the diameter of the "spot." The light guide 108 is flexible, and has one end 108a seated in this light guide port 308 and its other end 108b attached to the hand piece 109. There is an interlock switch 306 at the light guide port 307 which detects when the light guide 108 has been manually removed from the light guide port.

The light guide 108 comprises a clear plastic tube 108c holding a liquid, with a steel coil 108d wound about it to prevent the light guide from being bent excessively. Preferably, the radius of a bend should not exceed about 6 inches. This avoids kinking of the tube 108c. The tube 108c can be made of any of a variety of clear plastic materials. The plastic tube material must have a higher refractive index than the liquid it carries and be impermeable to that liquid. The dimensions of the tube 108c may range from about 2 to 14 mm in diameter and be from about 4 to about 10 feet long. The tube may be constructed of a plastic material such as fluoropolymer, for example, Teflon, or another halohydrocarbon polymer or polymers such as 4-methylpentene-1, polymethylpentene, polyvinyl chloride, polyethylene, or silicone. The plastics for the tube 108c must be stable to the visible light. It is desirable to use inside the light guide 108 a liquid material that conducts light efficiently, and preferably in excess of 70% of the visible light transmitted by the guide reaches the handpiece 109 and emanates from the tip 111. The liquid should not wet the inside surface of the tube 108c or be hygroscopic. To maximize light transmission, the refractive index of the liquid is somewhat lower than that of the material of the tube that contains it. Particularly preferred liquids include alcohols free of any water, as for example, methanol. Conductive materials may be dissolved in the liquid and suitable conductive materials include compounds of alkali and alkaline earth metal halides. Preferred among this group are hygroscopic salts such as calcium chloride, cesium chloride, cesium fluoride and magnesium chloride. It is also possible to use such salts as nitrates, phosphates, and other such conductive materials.

There is a fiber optic 104 that has an end located in the optical path at or near the opening 14 to collect a sample of light from the filters 102A and 102B. The fiber optic 104 has another end terminating at a radiant energy sensor 106, such as, for example, a Golay sensor, photodiode, cadmium-sulfide cell, pyrometer, pyranometer, or thermopile, which is connected through an amplifier 106a to the microprocessor 300. In response to the energy level of the sample of light collected, the fiber optic 104 provides a control signal to the master microprocessor 300. The microprocessor 300 in response to the control signal from the radiant energy sensor 106 regulates the voltage applied to the bulb 100 to adjust or maintain the energy output of the bulb substantially constant despite external fluctuations such as power source variations or internal fluctuations such lamp warm-up characteristics. The light energy from the bulb 100 tends to diminish over time. This is especially true during the first 60 seconds each time the bulb 100 is energized. By varying the voltage applied to the bulb 100 as required, this energy output can be maintained substantially constant.

A radiometer 202 is disposed in the control panel P which is used during manufacture for calibration and by the dentist to check the power density of the light emanating from the tip 111 and, if desired, calibrate the bulb 100. As used herein "radiometer" refers to a device for detecting light energy, inclusive of a photosensor that the light strikes and the associated electronics and readout. A suitable photosensor is sold by Hamamatsu Corporation under the part No. S1087.

During factory calibration as discussed in greater detail subsequently, the tip 111 is placed against a standard radiometer which has been calibrated to national standards. Assume, for example, that this standard radiometer indicates that the light energy output from the tip is 1000 mw/cm$^2$. The tip 111 is then placed against the surface of the radiometer 202. Assume, for example, that this radiometer detects a light energy output displayed on the display 204 in the panel P of 1100 mw/cm$^2$. The radiometer 202 is then adjust using its potentiometer (not shown) so that the readout on the display is 1000 mw/cm$^2$.

Important Features

The lamp apparatus 10 is equipped with an audible alarm or beeper 207 that indicates precise elapsed time periods so that the dentist will know how long light has been applied to the tooth being treated. The lamp apparatus' power inlet, fuses, and foot switch connector are on the underside 309 of the housing 20. As shown in FIG. 5, the lamp apparatus 10 is plugged into a D. C. power supply 505 under the control of the keyed on/off switch 310. After the lamp apparatus 10 is plugged into an electric outlet, the user, who may be a dentist or a hygienist, will turn the lamp apparatus 10 on with a key for the keyed on/off switch 310. The user will then select the desired operating mode, BLEACH or KURE, and proceed with either bleaching or curing. The tip 11 is then positioned adjacent the tooth being treated.

The housing is cooled by either an DC fan 503 or AC fan 504. If the DC fan 503 is used, it is switched by a transistor (not shown) connected to the microprocessor 300. If the characteristics of an AC fan are more desirable, such as price, power usage, velocity, or durability are better met by an AC fan, the AC 504 is used. It is switched by a thyristor (not shown) and electronic optical isolator (not shown) connected to the microprocessor 300.

The bulb 100 manifests very low 'cold' resistance, a small fraction of an ohm which increases to approximately 2.3 ohms within the first second after being energized. The bulb manufacturer advises that this can result in surge currents of over 140 amps upon application of power, possibly harming the power supply 505, or impairing its operation, as well as reducing bulb life, and requiring more expensive switching components. The lamp apparatus 10 uses an additional low-cost switching circuit which is switched on first, connecting the lamp apparatus to the power supply through a series resistor 100a (FIG. 5) of 1.5 ohms rated for 50 watts dissipation. The microprocessor 300 measures through the analog to digitial converter 88 the voltage at the power supply bulb terminal, then the switched bulb terminal, and by simple subtraction determines the bulb voltage. Upon obtaining at least 6 volts across the bulb 100, the microprocessor 300 signals a second switching circuit to bypass the resistor 100a, so that from then on the bulb voltage nearly equals the power supply voltage. This reduces the theoretical surge from 140 amps to maximum of 17 amps, or about 14 amps when taking into account the bulb, wiring and switching component resistance. Upon switching off the bulb 100, the main switching circuit is switched off but the starting circuit remains on, leaving the path through the resistor 100a connected. This improves the response of the power supply 505 which may otherwise react poorly when the entire load is removed, such as by its output voltage exceeding overvoltage protection. After a delay of 50–100 milliseconds the starting circuit is switched off.

Additional features that aid in convenience of use include an instant 'on' feature, automatic calibration at power up, an integrated power measurement system that allows the operator to verify power density using the radiometer 202, the microprocessor 300 control for continuous light energy output regulation, system monitoring, and status notification, a detachable curing tip 111 allowing steam autoclave sterilization, disposable protective sleeves (not shown) for the curing tip allowing quick turn-around between patients, a 3-digit LED display 204 for monitoring power density output and exposure time, visual and audio signals indicating exposure time, and other messages including error messages.

The lamp apparatus 10 of this invention integrates advanced optics with a light source, an incandescent bulb 100, that can deliver at least 1000 mw/cm$^2$. This is achieved by the use of a 150–600 watt xenon halogen light bulb 100 mounted in the dichroic reflector 101. This combination of bulb 100 and reflector 101 comprises the light source to achieve the power density required and to pass most of the infrared (IR) light back through the reflector 101 to avoid transferring the heat generated by the bulb 100 to the filters 102A or 102B or the light guide 108. Most of the light that is reflected by the reflector 101 is visible white light that is passed through the filters 102A or 102B to screen the appropriate wavelengths for curing or bleaching. Small amounts of infrared light are passed through to the liquid light guide 108, but this infrared light is absorbed by the liquid in the light guide over the length of the guide. The reflector 101 also focuses the light to an approximate spot size of about 8 mm. The 8 mm focused stream of light entering the liquid light guide 108 has a diameter size approximately equal the diameter of the guide of from about 2 to 14 mm. The liquid light guide 108 minimizes energy loss and maximizes energy. The inventors have devised this combination of bulb 100 and reflector 101 to achieve the power density required to cure restorative dental material in fifteen (15) seconds, or less. The image conduit 110 is made of optical-quality glassware. The image conduit 110 is part of the handpiece 109, which is detachable as necessary for sterilization.

The quality of light itself is substantially improved with all visible wavelengths, or colors, being transmitted equally well. The liquid light guide 108 transmits light more efficiently than a fiber optic bundle. Much of the curing light prior art use fiber optic bundles for light transmission. The reason that a liquid light guide 108 is more efficient for light transmission than bundles of fiber is due to packing loss. No matter how closely packed solid light fibers are, there is some packing loss. In fiber optics, light lost between fibers is known as packing loss. The light wasted by broken fibers is called spotting. These problems are avoided when the liquid light guide 108 is used.

Standard fiber bundles of borosilicate glass subtract blue light through absorption causing a "yellowing" of white light. This occurs as a result of the absorption of blue light. In addition, a small percentage of light at other wavelengths is absorbed for each foot of length in the fiber bundle. In this fashion, both total light and blue light are subtracted as light passes through the fiber bundle. This results in a more yellow light at the output end when compared with the true white light found at the end of a single quartz fiber or the liquid light guide 108 of this invention.

Further contrasting the liquid light guide 108 with the solid fiber optic bundle, the longer the fiber bundle, the more the light is degraded and diminished as it travels from light source to dental instrument. In contrast, the liquid light guide 108 will absorb very little visible light. As a result, a liquid light guide provides better quality illumination than bundled fibers for the purposes of the instant invention. Since the liquid light guide 108 is a totally conducting liquid, there is no such wasted space in the light-conducting tube of this invention. In the instant invention, the light-conducting liquid totally fills a clear tube that contains it. This is an inexpensive and efficient means of conducting light in the unit of this invention.

Microprocessor

There are two microprocessors in the lamp apparatus 10. The master microprocessor 300 is the PIC 16C74A, made by Microchip. It resides on the main control panel printed circuit assembly 300a and controls the operations of the lamp apparatus 10 in conjunction with the slave microprocessor 501, which is in the panel P. The slave microprocessor is the Microchip PIC 16C62A. An advantage of using the microprocessors 300 and 501 to control the lamp apparatus 10 is that they may be readily replaced with another microprocessor for repair, upgrading, or reprogramming of the lamp apparatus 10.

Figure 6:
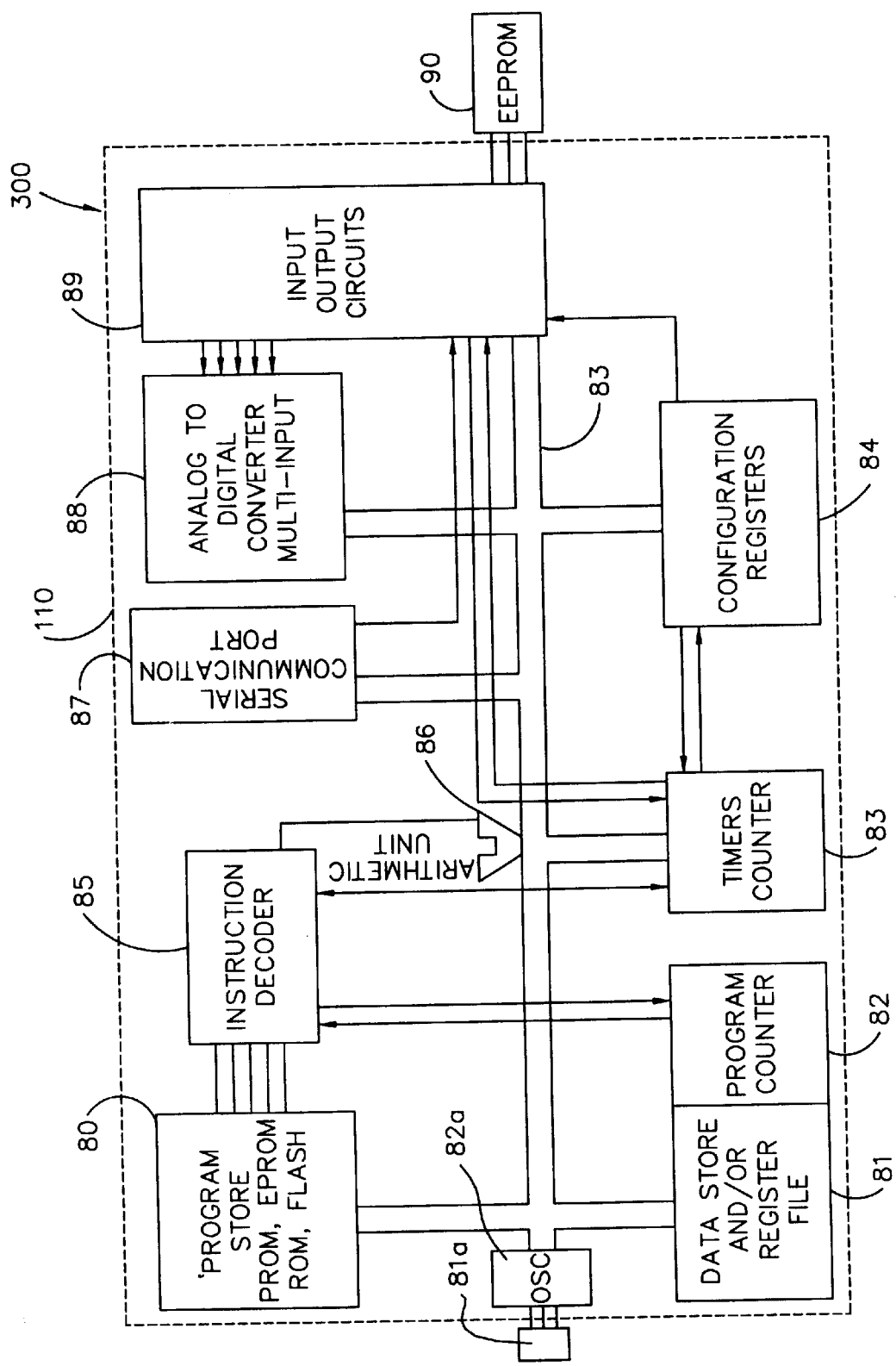
FIG. 6 is a schematic block diagram of the main central microprocessor circuit used in the dental lamp apparatus of the present invention.

As illustrated in FIG. 6, the master microprocessor 300 includes a (not shown) to which are electrically connected the major components of the microprocessor. These components include a program storage memory 80 having memory components such as a PROM, ROM, FLASH, data storage memory 81 including various registers, a program counter 82, utility timers and counters 83, configuration registers 84, instruction decoder 85, arithmetic unit 86, serial communication port 87, an analog to digital converter 88, and input/output circuits 89. An EEPROM 90 is connected to the microprocessor 300 through the input/output circuits 89.

There is an external crystal resonator 81a connected to an internal oscillator 82a which determines the rate of execution of instructions for the program. The oscillator 82a further provides the time base required by the utility timers and counters 83, serial communication port 87, and analog to digital converter 88. The EEPROM 90, which provides a non-volatile read-write memory, is connected between the I/O circuits 89 and the slave microprocessor 501, which may be connected at either of the two locations corresponding to cable 1 or cable 2.

Program

Figure 4:
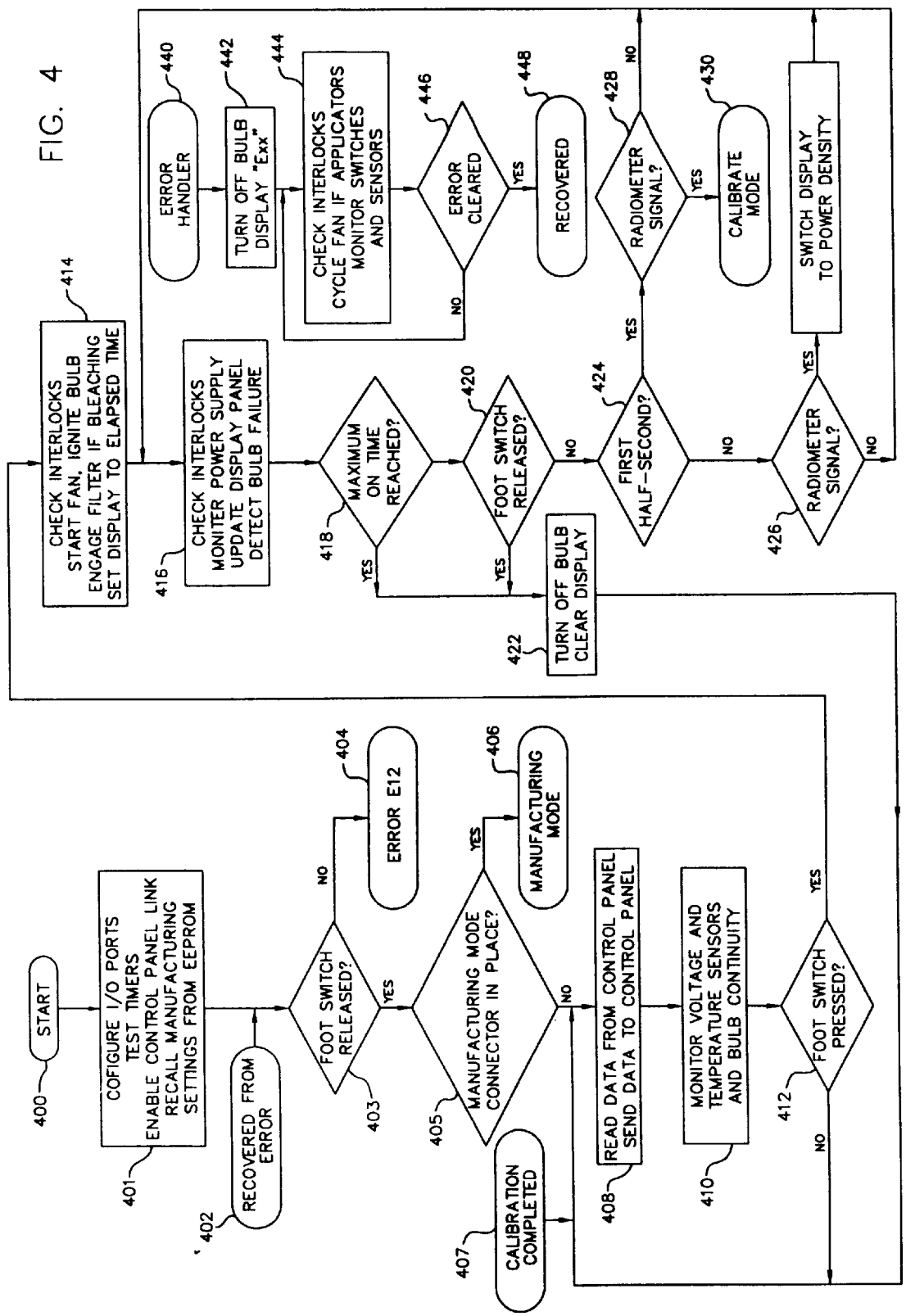
FIG. 4 is a flow chart of the program for the master microprocessor for controlling the lamp apparatus' operation.
Figure 4A:
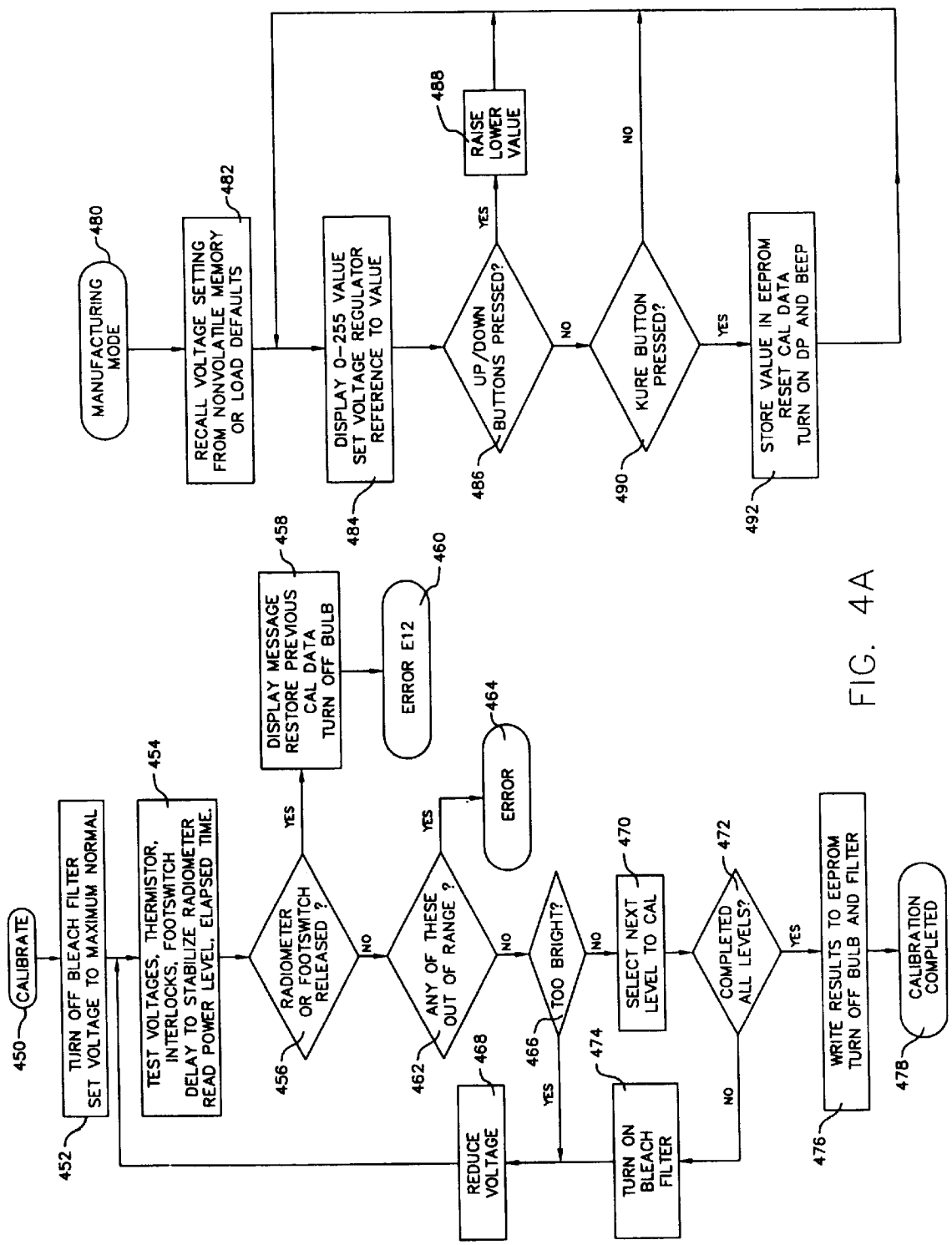
FIG. 4A is a flow chart of the program for adjustments made when automatic bulb calibration is performed, or for adjustments made during manufacture of the lamp apparatus.
Figure 7:
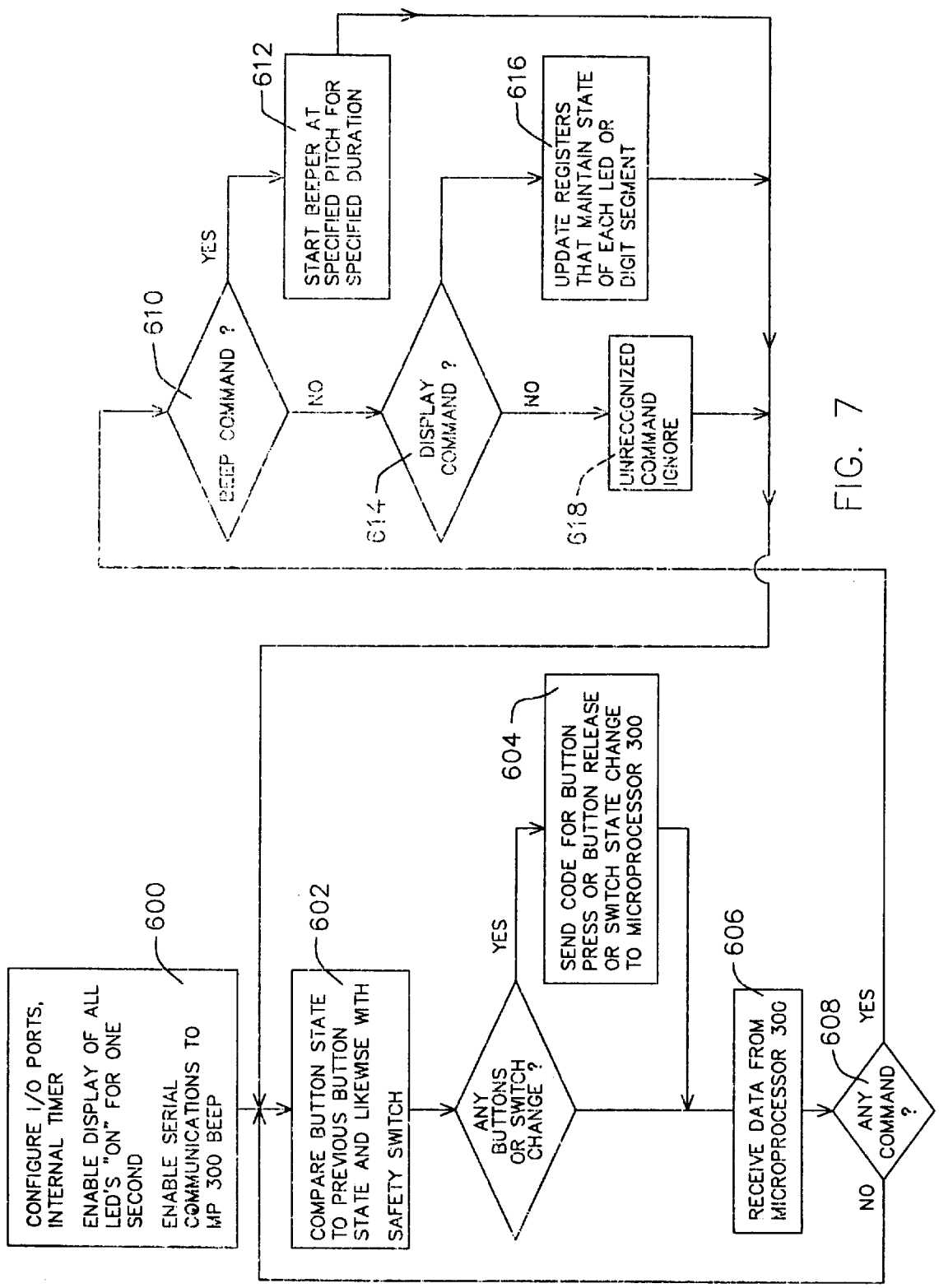
FIG. 7 is a logic flow diagram depicting the routines of the program for the slave microprocessor housed in the control panel of the lamp apparatus.

The program routines for the master microprocessor 300 are represented by the logic flow diagrams of FIGS. 4 and 4A and the program routines for the slave microprocessor 501 are represented by the logic flow diagram of FIG. 7. These routines shall be discussed in connection with the control circuit 200 shown in FIG. 5.

In the start-up routines 400 and 401, the microprocessor 300 powers up several registers (not shown) and latches (not shown) which are set to standard settings determined by the microprocessor's manufacturer. The firmware in microprocessor 300 configures I/O circuits 89 and timer 83 needed to respond to detector interlock switches 305 and 306, thermistor 508, and radiant energy sensor 106 and issue control signals for the lamp apparatus 10. User settings and baseline condition variables are set to starting values. The control panel link through cable 1 or cable 2 is established to connect the master microprocessor 300 and slave microprocessor 501, setting their communication ports to a common protocol and data speed. At this point the nonvolatile memory EEPROM 90 is scanned for a signature indicating that the lamp apparatus' data have been correctly stored. These data include factory settings, bulb 100 calibration voltages for each operating mode, KURE or BLEACH, lamp lifetime registers 81, and the like. These data are recalled and placed in working registers 81 to be used by the program for the microprocessors 300 and 501.

The initial state of the detector interlock switches 305 and 306, thermistor 508, and radiant energy sensor 106 is determined by the microprocessor 300 and compared to acceptable values. The program also monitors the state of the solenoid 103, and sets power supply control for the bulb 100 to 16–25 volts, as well as monitoring the interlock switches 305 and 306. Interlock switches 305 and 306 are in place to prevent accidental activation of the lamp 10. If the panel P is removed while bulb 100 is energized or the dentist accidentally activates either the footswitch 509 or trigger switch 509A while the panel is disconnected, the bulb 100 cannot be energized. Similarly with the interlock switch 306 indicating that the light guide 108 has been disconnected, the bulb 100 cannot be energized or is deenergized, if turned on. The thermistor 508 starts the fan 503 or 504 if excessive temperature is detected, but if the interlock switch 305 indicates that the panel P has been disconnected, the fan 503 is stopped or prevented from starting as a safety feature.

According to routine 403, with the footswitch 509 depressed (or trigger switch 509A if used instead of the footswitch), an error identified by the notice "E12" is displayed on the display 204 and the program switches to an error handler routine 440 via routine 404. The error handler routine 440 via routine 442 turns off the power to the bulb 100 and displays on the display 204 a notice, for example, "E01" for bulb failure. The error handler routine 440 will also display other error messages on the display 204 concerning failure of the bulb 100, fault in power supply 505 (FIG. 5), errors in the thermistor 508, failure of the solenoid 103, failure of drivers 507 (FIG. 5), EEPROM 90 memory failure, failure to pass processor self test, radiometer 202 failure, or serial communication port 87 failure, If the error condition has been cleared, and this has been detected in accordance with routine 446, control is again transferred to the routine 403 via the routines 448 and 402.

Upon start up without the footswitch 509 pressed (or trigger switch 509A if used instead of the footswitch), in accordance with routine 405, the microprocessor 300 is tested for the presence of a connector 510. When in the manufacture mode, a manufacturing technician adjusts the voltage applied to the bulb 100 by first connecting the microprocessor 300 to the shorting connector 510 which engages two or more pins (not shown) of the input/output circuits 89 of the microprocessor 300. The microprocessor 300 is then accessed by the technician to input values needed for the operation of the lamp apparatus 10 but not needed by the user.

One of the input/output circuits 89 is read to determine the absence or presence of the shorting connector 510. If the output is high this indicates the absence of the shorting connector 510. If low, the shorting connector 510 is connected to the microprocessor 300. With the shorting connector 510 present, control is transferred to manufacturing mode routine 480 shown in FIG. 4A. First routine 482 either provides for the loading of values in the non-volatile memory of the EEPROM 90 or recalls already stored values from the non-volatile memory of the EEPROM. Next the routine 484 displays on the display 204 a binary number from 0 to 255 which is retrieved from the EEPROM 90. This value represents the count received when reading 0.1 volts more than the maximum analog input voltage to the bulb 100, nominally 26.1 volts. This value is never used during bulb operation, but is used as a ceiling so that the program may detect having exceeded its proper operating value.

The program insures that the maximum voltage delivered to the bulb 100 is reduced from this amount by at least 0.1 volts, so that when accounting for wiring and switching components the preferred 24 volt bulb 100 never receives more than 8% starting over-voltage allowance designed-in by the manufacturer. The technician uses the up/down buttons 203 to make the appropriate adjustments in values via the routines 486 and 488. The routine 484 also sets the voltage regulator (not shown) as discussed subsequently in greater detail. The technician then presses the KURE button 200B to initiate the routine 490 which then displays a decimal point (DP) on the display 204 and activates the beeper 207 (FIG. 5), indicating that the inputted values are stored. The program will at this stage indefinitely continue to process routines 482 through 492 until the on/off switch 310 is turned off.

Voltage control and regulation are accomplished through a combination of processes. Power is converted from a universal AC input (100–240 volts nominal, 50–60 cycles per second) to a single adjustable output of approximately 24 volts DC. Line regulation nearly eliminates fluctuations in the output that would be associated with changes in AC input voltage. Load regulation minimizes changes in output voltage that would be expected to occur as inverse function of the 0 to 12.5 ampere operating current.

The power supply 505 is a Mean Well, Inc. Part No. SP-300 which includes a provision for output adjustment usually accomplished by a technician using a screwdriver, or by disabling this control and utilizing an electronic control path 506 (FIG. 5) through which a small current of approximately 0.5 milliamperes to 1.5 milliamperes produces an output voltage of 16 to 27 volts. The control current has less than an ideal response. For example, there is no reduction below 16 volts for any current from 0 to 0.5 milliamperes, the 24 volt level is reached at 1.25 milliamperes, and the last 0.25 milliamperes swings the rest of the way to 27 volts. Power supplies are available to produce a more desirable response but as this tends to be a feature of precision or laboratory power supplies. Such power supplies could easily cost more alone than the entire lamp apparatus 10. Therefore, it is a feature of the instant invention that the response of the low cost power supply 505 and low cost electronic control path 506 are collectively stabilized using a simple voltage regulator algorithm. One of the channels of the analog to digital converter 88 of the microprocessor 300 receives a fraction of the power supply voltage using a simple resistance divider of 22 K ohms and 4.7 ohms, so that the sampled voltage is within the input range of the analog to digital converter 88.

When FIG. 4A references a "voltage regulator," the program simply stores a numeric value in one of the resisters 81 of the microprocessor 300. This numeric value is compared to the value returned from the analog to digital converter 88 approximately 20 times per second. One of the timers 83 of the microprocessor 300 is configured during the routine 401 to generate a pulse-width modulated output. The output is fed through a resistor, capacitor, and transistor (not shown) to convert its duty cycle to a DC current in the range stated above. If the value read from the analog to digital converter 88 input representing the voltage is less than the value stored in the register 81, the microprocessor 300 increases the value in the timer 83 to increase the duty cycle. Likewise, if the voltage is greater than the desired value, then microprocessor 300 stores a reduced value in the timer 83 to reduce the duty cycle.

Assuming the shorting connector 510 is disconnected from the microprocessor 300 and power is removed and then reapplied to the lamp apparatus 10, the program again starts routine 401. The program now reads data from the control panel P and sends data to the control panel via the routine 408 and monitors idle conditions such as bulb voltage, the thermistor 508, and bulb continuity via routine 410.

Bulb continuity check:

An extremely low cost circuit detects bulb 100 failure. A 22K ohm and 4.7K ohm resistor (not shown) from a voltage divider identical to the one used for monitoring the power supply voltage as described above is connected to another one of the several inputs of the analog to digital converter 88 in the microprocessor 300. One of the bulb 100 terminals (not shown) is wired directly to the positive terminal of the power supply 505. The other bulb 100 terminal is wired to the switching components (not shown), the 1.5 ohm 50 watt resistor 100a used for the soft-start, and to the 22K/4.7K divider (not shown). The bulb voltage is monitored at both bulb terminals. When the bulb 100 is off, the voltage should be the same at both bulb terminals, within the few percent tolerance of the resistors. The microprocessor 300 periodically samples both inputs to the analog to digital converter 88 while in program routine 410, and upon finding a very low reading of the analog to digital converter 88 representing a lack of voltage at the bulb 100, an E01 error is produced to signal a lack of continuity, so that the operator may check for a loose or burned-out bulb 100.

Bulb failure check:

The above method will not work while the bulb 100 is switched on, because the switching components (not shown) and resistor are returned to the negative side of the power supply 505, so that this bulb terminal has nearly zero volts present as readable by the analog to digital converter 88. Upon bulb failure, this bulb terminal will still have zero volts present, so there would be no difference in the reading. Therefore, the high speed of modern switching components is exploited so that approximately once per second the electronic switch (not shown) such as the HexFET RFP50N06 made by Philips Semiconductor Corporation, switches off for a period of approximately 50 microseconds, allowing ample time for the voltage at bulb 100 to return to the same level as its off state, so that microprocessor 300 may receive from the analog to digital converter 88 a value of only 0 to 1 (out of 255) indicating a bulb failure, or a higher value indicating proper operation of the bulb 100.

The program responds to commands produced by manipulation of the buttons 200A and 200B. Pressing 200A while already in the BLEACH mode advances to the next power level. If the lights 201 indicate "normal' power level, pressing 200A advances to "boost," and if in "boost," to "ramp," and if in "ramp" to "normal." The same in true when in the KURE mode.

The microprocessor 300 is programmed to require a new transition of the footswitch 509 (or trigger switch 509A if used instead of the footswitch) each time the bulb 100 is energized and deenergized. In this manner accidental triggering of light output is prevented. If no new footswitch transition is detected in accordance with routine 412, the program continues to cycle routines 408 through 412. If a new footswitch press is detected in accordance with routine 412, the program advances from routine 412 through routine 420. Routine 414 checks the interlock switches 305 and 306, starts the fan 503 or 504, turns on the bulb 100, activates the solenoid 103 if in the BLEACH mode to position the bleaching filter 102A, and initiates the display of numbers in the display 204 corresponding to the elapsed time that the bulb is energized. The display 204 is initialized to 00 seconds and set to maintain an updated display of elapsed time.

Routine 416 continues to check the interlock switches 305 and 306, monitors the D. C. power supply 505, updates the readout on the display 204, and detects bulb failure as discussed above. As a safety feature, routines 418 and 422 deenergize the bulb 100 if it is maintained on for a prolonged time period (for example, when the bulb 100 has been left on for more than 4 minutes in the KURE mode or 30 minutes in the BLEACH mode), or if the fan 503 fails to operate or the air intake or exhaust is blocked. The thermistor 508 is a fast-acting type positioned in the air stream and receives some of the internal light that could not be productively steered to the light guide 108. It will nominally remain cool but will quickly reach 80 degrees Centigrade if the air intake is insufficient to offset the received light energy, for example, if the fan 503 or 504 fail or an air intake (not shown) is blocked. Release of the foot switch 509 via routines 420 and 422 returns the program to repeat the routines 408 through 422. The routine 422 turns off the bulb and clears the display.

The following various operational problems or errors will switch the program over to the error handler routine 440. If the panel cable 1 or 2 is disconnected, the microprocessor 300 senses incorrect signal polarity at the serial communication port 87 and goes into the error handler routine 440 with EOS, turning off or suppressing operation of bulb 100, though the EOS will of course not appear at the panel if the cable 1 or 2 is completely disconnected, but only if the data wire from the panel is disconnected and power wires and sufficient data wires to the panel remain intact for the display to function. The bulb voltage, interlock switches 305 and 306, and thermistor 508 are monitored in accordance with routine 410. The DC fan 503 or AC fan 504 is started if excessive temperature is detected by the thermistor 508. The DC fan 503 or AC fan 504 may still be running as a result of bulb use in accordance with routine 414. In either case, the fan elapsed time is monitored and the fan 503 is shut off after 3 minutes. The fan is shut off by time rather than temperature since the thermistor 508 is in the air stream and will fall below the temperature level at which it is turned on within a few seconds. If the temperature remains excessive after the fan has been on for 3 minutes, the thermistor 508 will again respond to this condition within seconds.

The radiometer 202 is tested by the microprocessor 300 so that either the power density is displayed on the display 204, or automatic calibration of the bulb 100 will be accomplished depending on how long it has been lit. If the bulb 100 has been lit for one-half second or more in accordance with routine 424 and a radiometer signal is detected in accordance with routine 426, the display 204 will indicate power density in watts/cm2. If the bulb 100 has been on less than one-half second and a radiometer signal is detected in accordance with routine 428, control is transferred to the calibration mode 450 (FIG. 4A) which is discussed subsequently in greater detail. If no signal is detected from the radiometer 202 in accordance with routines 426 or 428, the bulb 100 remains lit and control of the lamp apparatus 10 continues through routine 416.

The up/down buttons 203 perform multiple functions. As discussed previously, the up/down buttons 203 raise or lower manufacturing settings at the factory. The buttons 200A and 200B rotate through the six possible curing and bleaching modes. If the startup procedure is successfully completed and the footswitch 509, or alternately trigger switch 509A on the handpiece 109, is activated and calibration is transferred to routine 450 (FIG. 4A) via routine 430. FIG. 4A illustrates the logic flow of the calibration mode for using the radiometer 202. On entry to calibration routine 450 in accordance with routine 430 (FIG. 4), the bleach filter 102A is turned off (if it was on) and the power supply 505 is set to the maximum voltage allowed for the KURE mode, normal power level in accordance with routine 452.

An iterating process begins in accordance with routine 454 which monitors power supply 505 voltages, interlock switches 305 and 306, thermistor 508 levels, footswitch 509 and radiometer 202 signals. If the footswitch 202 is released or the radiometer signal drops below 150 mw/cm2, as detected by routine 456, the user is terminating calibration so a message such as E14 is displayed on the display 204 indicating an incomplete calibration, the bulb 101 is turned off, previous calibration data are read from the EEPROM's 90 nonvolatile memory, and control is restored to the main loop routine 408 (FIG. 4) in accordance with routines 460 and 407.

If voltages are invalid, temperature is excessive, interlock switches 305 or 306 are violated, or elapsed time indicates calibration has taken longer than 30 seconds, or bulb 100 output is too low in accordance with routine 462, an appropriate error message is issued in accordance with routine 464 and control transfers to the error routine 440.

If the power density is excessive, for example, more than 1,100 mw/cm2 for the KURE mode, normal power level, BLEACH mode, normal power level, in accordance with routine 466, the voltage to the bulb 100 is reduced in accordance with routine 468 and the cycle continues to routine 454.

If the power density is not too low in accordance with routine 454 and not too high in accordance with routine 466, then the next bulb output power level to be calibrated is selected in accordance with routine 470. If the next power level is to be calibrated, in accordance with routine 472, the bleaching filter 102A is engaged or remains engaged in accordance with routine 474, and the voltage is reduced in accordance with routine 468 and measurement continues with routine 454. If the last power level has been calibrated in accordance with routine 472, the voltage levels for the CURE mode, boost power level, CURE mode, normal power level, BLEACH mode, boost power level, BLEACH mode, normal power level, are stored in the EEPROM in accordance with routine 476, and the calibration process ends, turning off the bulb 100 and bleaching filter 102A in accordance with routine 478, and returning to standby in accordance with routine 407.

The lamp apparatus 10 has this "calibrate-on demand" feature that may be used on a maintenance basis or if the dentist senses a problem. The calibration procedure requires the dentist to steadily hold the flat surface of the curing tip 111 flush against the front panel radiometer 202. The dentist then presses and holds the footswitch 509. The display 204 will read "CAL" for 10–20 seconds. When calibration is complete, the LED display will read "ON".

During calibration, the microprocessor 300 is in calibration routine 450. The lamp apparatus 10 may display a "CAL" message may momentarily when the lamp apparatus is turned on by switch 310. This indicates that calibration is recommended. This warning also appears after a bulb 100 has burned out. The "CAL" message stops after the bulb 100 has been successfully calibrated.

If there is insufficient power density during calibration, the display 204 will indicate error code E03, and then "on". This indicates that the bulb 100 needs replacement or that the tip 111 was not held accurately over the center of the radiometer 202 or the light guide was no seated, or debris is interfering with the optical path A. If either of these errors occur, the bulb 100 may still be used, but its light output may vary from the desired levels. The "Verify-on-Demand" procedures measure the power density. If the power density output is higher or lower than expected, the dentist may decrease or increase patient exposure times accordingly The Verify-on-Demand feature of the lamp apparatus 10 may be used to verify the power density at any time. To perform this function the dentist must hold the curing tip 111 away from the front panel radiometer 202, press the footswitch 509, then wait one second. The curing tip 111 is moved to the radiometer 202 target to verify the power density which is in units of watts/cm2. It is recommended that a verification be performed if there is a question or concern concerning performance or power density.

Routine 430 indicates that the full calibration state is entered. To enter, the dentist must both press the foot switch 509 and have the curing tip 111 positioned at the front panel P calibration target. In the calibration process, the bulb 100 is turned on and the voltage is brought up until the detected and displayed power density reaches 1.00 watts/cm2 (or 1000 mw/cm2) with a tolerance of +10%–20% for a period of three seconds. The bulb 100 voltage is then raised until the maximum bulb voltage for "normal" power level curing is reached. The detected and displayed power density is greater than or equal to 0.80 watts/cm2 (800 mw/cm2) and less than 1.00 watt/cm2, with the same error tolerances as stated above, for a period of three seconds. Following the successful calibration of the bulb 100, the program next reduces the bulb voltage. After stabilizing, the dentist is ready to execute bleach or cure.

The program routines for the slave microprocessor 501 are represented by the logic flow diagram of FIG. 7, and they are designed to signal the master microprocessor 300 in accordance with the operation of the buttons 200A, 200B, 203. Individual segments of the display 204 and the warning lights 205 and 206 and power level indicator lights 201 are illuminated in accordance with instructions from the program from the microprocessor 110 which are forwarded to the slave microprocessor 501.

The routine 600 configures output ports for the LED display drivers (not shown), and input ports for the buttons 200A, 200B, 203. The routine 600 further sets the timing functions (a) for serial communication with the microprocessor 300, and (b) for the rate at which display digits are multiplexed and button states are sampled. In routine 600 all the LEDs are enabled and lit for one second so that the user may observe that they are functional. The beeper 207 is also briefly activated so that the user may observe that it is functional and that power has been turned on.

The routine 602 compares the current state of the buttons 200A, 200B, 203 to a previous state sampled several milliseconds earlier, preferably from about 10 to about 20 milliseconds. If there is a change in the button state, a predetermined numeric code identifying which individual button has changed state and whether the the button is activated or deactivated. This information is transmitted from a serial port (not shown) on the slave microprocessor 501 to the serial port 89 of the master microprocessor 300. Signals from the master microprocessor 300 are forwarded to the slave microprocessor 501 independently of receiving updated information from the slave microprocessor. In routine 606 the master microprocessor 300 transmits a signal to either activate the beeper 207 or signals to update anyone or all of the LED's of the display 204 via the routines 610, 612, 614, 616, and 618.

Bleaching/Whitening

For bleaching, the lamp apparatus 10 is powered-up and calibrated as has been described above, and then the tooth having a bleach applied thereon is irradiated. Commercial dental bleaching agents, as for example Superoxol, are available for this purpose. Superoxol is a 30% aqueous solution of hydrogen peroxide. The commercially available peroxides for dental bleaching include activator powder such as silica. When irradiated with light, the temperature of the bleaching agent is elevated and the bleaching process is enhanced.

For bleaching operations, the dentist depresses the "bleach" button 200A on the control panel P. This activates the filter 102A and light having a wavelength of 400–550 nm is focused on the entry end 108a of the liquid light guide 108 and then transmitted through the handpiece 109 to the tip 111. The 400–550 nm wavelength range light activates the peroxy (—OOH) ion used in bleaching. This wider wavelength range also allows more heat transmission. The additional heat is beneficial for the bleaching process.

When light of 400–550 nm is shined on the peroxide solution, the temperature transmitted to the tooth rises as the solution breaks down. During the bleaching process of this invention, the temperature has been measured at a maximum of about 130 degrees F. This temperature, while warm, is not uncomfortable to the patient for the short amount of time the bleaching is performed.

The time for total whitening for the process of this invention is greatly shortened from what has been reported previously. The time for whitening is reduced in the current invention to about 3 minutes per tooth. This bleach time translates into about three applications of bleach/activator/indicator followed by about three irradiations of light for about one minute. For each arch of six teeth being bleached, about 18 minutes will be needed for completion.

The lamp apparatus 10 has the three power levels for both curing and bleaching: normal, boost, and ramp. When "normal" power level is selected, the power available is from 500–1000 mw/cm². At the bleaching "normal" power level, the bulb 100 turns on at +16 V and rises to the adjusted calibrated voltage to reach 1200 mw/cm2 (+10%, -20%) at a rate of 4.5 V per second.

At the boost power level, the energy available is from 800–2000 mw/cm². This power level offers a higher level of energy than is available under normal conditions. The bleach boost power level is used when extra power is needed, when faster activation is desired, or when bleaching badly stained teeth. The bleach boost power level starts at +16 V and rises to the adjusted calibrated voltage to reach 1500 mw/cm2 (+10%, -20%) at a rate of 4.5 V/second.

Curing

If the dentist desires to cure restorative dental materials, he or she depresses the button 200B and the filter 102B will be activated. The wavelength of light used will then be 400–500 nm to cure a restorative dental material of 2 millimeters (mm) in about 15 seconds, typically 10 seconds or less. This time is four (4) times the rate of conventional dental light systems. It is about as quick as that of a laser or a high-powered VLS instrument.

When the button 200B is pressed, the filtered light cures essentially all photo-activated dental materials. Included in this group are those materials used in direct restorations, sealants, bonding agents, primers, and the like. The normal power level has a power density of nominally 1000 milliwatts per square centimeter. The curing time for 2 mm thickness curing material does not exceed about 15, typically 10 seconds, for a full curing cycle when the bulb 100 calibrates to 1000 milliwatts/cm2 (+10%, -20%) output.

If the lamp apparatus 10 is set to the normal KURE mode by depressing the button 200A, the indicator 201 reads normal. The footswitch 509 must be pressed to initiate the curing cycle. The curing tip 111 should be placed a distance d of about 4 mm or less from the tooth surface that is being treated. The lamp apparatus' beeper 207 will "beep" at the beginning of a cycle and every 5 seconds thereafter. When operating at normal power level and set for curing, the lamp apparatus 10 typically produces a 10 second cure in dental resin to a depth of about 2–4 mm, with the filter 102B passing light of a wavelength from about 400 to about 500 nm.

If the lamp apparatus 10 is set at the boost power level by depressing the button 200B, the cure rate will increased by approximately 20% from the normal KURE mode. The boost power level may be used when extra power or faster curing is desired, when curing darker restorative dental materials, for bulk curing, quick 'tacking' of veneers, or if the dentist desires a greater depth of cure. Boost power level has a power density of up to 2000 milliwatts/square centimeter. For the boost level, this power density is increased by about 20% above the normal power level.

At the ramp power level, the dentist simply selects which of the several pre-programmed patterns of power density changes he or she desires by manipulation of buttons 203. Each restorative material to be activated has its own manufacturer's recommendations for curing times. When curing, the ramp power level typically increases the energy from a low to a high output level over a specified time period, but any desired pattern of change in power density may be provided depending on the type of material being cured. At the ramp power level, the power density is, however, usually gradually increased. Preferably, the selected "ramp" power level best matches the changes in light power density called for to enhance the physical characteristics of the specific cured dental restorative material being used. As discussed above, these changes in power density will correspond to those suggested by the manufacturer of the restorative material. Published papers, for example, Mehl et al in "Physical Properties and Gap Formation of Light-Cured Composites With and Without Self Start-Polymerization," Journal of Dentistry, Vol. 25, pp. 321–330, (1997) indicate that ramping provides more complete polymerization of restorative dental material. Leinfelder discusses the benefits of intermittent polymerization in his article on "New Developments in Resin Restorative Systems in JADA," Volume 128, May 1997. He discusses that a short light exposure time followed by darkness optimizes cure of the resin. This is more evidence concerning the utility of the ramp power level of the instant invention.

Examples

In the examples which follow, specific cases of bleaching and curing using the lamp apparatus 10 and methods of this invention are presented. The various parameters and conditions for the methods achieved using the lamp apparatus 10 of this invention are disclosed. These examples are meant for illustrative purposes only and are not intended to limit the instant invention in any manner whatsoever.

Bleaching

The dentist should consider certain factors important when selecting patients for bleaching. Those patients with yellow-brown stains of extrinsic origin will respond to the bleaching process of the instant invention with the fastest and best results. Tetracycline stains, fluorsis, and intrinsic mineral/metal stains are the most difficult.

Normally, teeth may be classified in the following Vita shades: A is brown discoloration, B is yellow discoloration, C is green discoloration, and D is red discoloration. Each of these categories of discoloration is then classified on a numerical scale with lower numbers indicating less discoloration and higher numbers indicating more discoloration. It is therefore an object of the bleaching procedures to grade the tooth color the lowest number possible.

It is usually the case that patients with A (brown) coloration will have the best results of color improvement. Patients with known thermal sensitivity, exposed dentin, large pulps, or leaking margins are not ideal candidates for bleaching for this process or any other bleaching process. Application of the bleaching treatment are also contraindicated if the patient has anesthetized teeth. Contraindications would also include porcelain crowns in notable positions in the arch. There is no whitening of porcelain crowns by this or any other bleach substance or process available.

Patient Preparation for Bleaching:

1. The teeth are cleaned on labial and lingual surfaces with pumice. After this, they are rinsed well.
2. The tooth shade is measured and recorded using the standard technique of comparing the patient's tooth shade with standard Vita shade samples.
3. After recording the tooth shade, snip open the ampule of gingival protectant. This is an orange gel that is commercially available as Charisma by the Confidental Company. The orange colorant enables distinguishing the gums from the teeth. The protectant also absorbs heat which is generated by the bleaching process.
4. Apply the protectant to the gingiva surrounding the teeth that are to be bleached.
5. Carefully apply a properly punched and sealed rubber dam to the teeth selected for bleaching. Ligation of teeth is recommended but is not necessary if the bleaching gel is sufficiently thick.
6. To mix the bleaching gel:
    a) Open the activator powder. For two separate mixes, pour the powder into the extra cup and seal with lid.
    b) Open the peroxide ampule by holding the ampule between the thumb and forefinger so that the tip is not pointed toward a person. Without squeezing the contents, carefully snip the sealed tip.
    c) Gently squeeze the ampule to dispense a portion of the peroxide into the activator powder and mix with spatula.
    d) Dispense enough peroxide to achieve a smooth, creamy, shiny consistency. One ampule is sufficient to treat one arch.
7. To apply the fresh bleaching gel mixture immediately to the patient, the following procedure should be followed. Gingival protectant, rubber dam, and protective eyewear should all be in place on the patient.
    a) Using an applicator brush, place a 2 mm thickness of activated bleaching gel on both the facial and lingual surfaces of the teeth. Care must be taken to not force bleaching gel over the tooth-rubber dam seal.
    b) With the instant unit set on BLEACH mode by pressing 200A, the practitioner will depress the footswitch 509, or alternately the trigger switch 509A. The dentist will then hold the handpiece 109 so that the curing tip 111 is approximately 3 mm from the tooth surface for about 60 to 90 seconds. The intensity of the light energy may be varied by changing this distance. The audible beep from the beeper 207 is heard every 5 seconds to facilitate time measurement.
    c) The light generated by the lamp apparatus 10 stops every minute when BLEACH mode is employed. If desired, the footswitch 509 can be again depressed to activate the lamp apparatus 10 and continue the bleaching process.
    d) If more whitening is desired after one application, the gel should be wiped off the entire arch and the procedure repeated.
8. When the whitening is satisfactory, the gel should be suctioned from around the teeth, and the rubber dam removed

Case Studies

Example 1 (Bleaching)

For a Caucasian male patient of 55, the initial tooth color was rated 3.5 A.

Six teeth were treated on the lower arch. Before mixing and applying the bleaching gel, the patient's gums were coated with Charisma gingival protectant. A dam was applied and cured with filtered light passing through the filter 102A to cure the dam. This light was used for about 10 seconds per tooth for a total of about 60 seconds (1 minute) to cure the dam on the lower arch of this patient.

When the dam was finished curing, bleach solution was applied to the front of the 6 teeth in patient's maxillary arch with a small applicator brush. The BLEACH mode selection by pressing button 200A to use filter 102A and the normal power level of the light was selected and applied. The bleach was 35% hydrogen peroxide solution.

The curing tip 111 was brought to about 4 millimeters from each tooth of the patient's lower arch for a total time of three minutes per tooth. The light automatically stopped every minute. At this time, the dentist checked the bleaching process was completed.

When the bleaching procedure was completed, the final shade was 2.0 A as measured on the Vita scale.

Example 2 (Curing)

The patient in this case was a 27 year old Caucasian female with a fractured maxillary lateral incisor. The cavity preparation material utilized for repair was a Microhybrid composite sold under the same of Herculite by the Kerr Corporation. The material was placed in the tooth.

To initiate the curing cycle, the footswitch 509 was pressed. KURE mode was selected by pressing mode selection button 200B. Normal power level was indicated by 'normal' light being on power level indicator 201. The beeper 207 beeped initially and continued to beep every 5 seconds thereafter. The exposure time was displayed on the LED display 204 in seconds. The handpiece 109 was lifted off the handpiece holder 308. The curing tip 111 was positioned approximately 4 mm from the restorative dental material.

For this curing example, the manufacturer's recommendations for curing the restorative dental material was 40 seconds. The light was activated for 10 seconds. The 10 seconds represent the full curing cycle. The restorative dental material was completely cured and hardened in 10 seconds.

Scope of the Invention

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A lamp apparatus including
    a handpiece having a tip,
    a light bulb positioned within a reflector which focuses light from the bulb at a predetermined point along an optical path,
    a filter along said optical path in advance of said predetermined point through which a predetermined wavelength of light in the visible range passes, and
    a flexible light guide between the handpiece and said predetermined point which transmits the light of said predetermined wavelength to the tip from which said light emanates,
    said bulb, when energized, emitting light of sufficient intensity so that the light emanating from the tip has a power density of at least 800 milliwatts per square centimeter, and, after filtering, having a wavelength of from 400 to 550 nanometers.

2. The lamp apparatus of claim 1 where the bulb has an enclosure holding a mixture of xenon and halogens and at a predetermined applied voltage emanates light having a power of 250 watts or greater.

3. The lamp apparatus of claim 2 where the applied voltage is 24 volts.

4. The lamp apparatus of claim 1 where the power density of the light emanating from the tip is from 800 to 2000 milliwatts per square centimeter.

5. The lamp apparatus of claim 1 where the reflector has an ellipsoidal configuration with a longitudinal axis coincident with the optical path and a focal point along the optical path.

6. The lamp apparatus of claim 5 where the bulb has an elongated filament disposed axially along the longitudinal axis, said filament, when the bulb is energized, providing at one section thereof light which is brighter than at other sections of the filament, said one section being near or at said focal point.

7. The lamp apparatus of claim 1 where said reflector is of the dichroic type which passes infra red radiation through the reflector.

8. The lamp apparatus of claim 1 where there are a plurality of filters which are selectively moved into the optical path to vary the wavelength of light being transmitted to the tip of the handpiece.

9. The lamp apparatus of claim 1 wherein the energization of the bulb is controlled by a manually operated activation switch.

10. The lamp apparatus of claim 9 wherein the activation switch is either a footswitch or a trigger switch connected to the handpiece.

11. A lamp apparatus including
    a handpiece having a tip,
    a light bulb positioned within a reflector which focuses light from the bulb at a predetermined point along an optical path,
    a filter along said optical path in advance of said predetermined point through which a predetermined wavelength of light in the visible range passes,
    a first mode of operation for bleaching of teeth and a second mode of operation for curing of light activated dental restorative material,
    a flexible light guide between the handpiece and said predetermined point which transmits the light of said predetermined wavelength to the tip from which said light emanates,
    said bulb, when energized, emitting light of sufficient intensity so that the light emanating from the tip has a power density of at least 800 milliwatts per square centimeter.

12. The lamp apparatus of claim 11 where in each of mode of operation there are a plurality of power levels.

13. The lamp apparatus of claim 11, when in the first mode of operation for bleaching of teeth, the filtered light has a wavelength of from 400 to 550 nanometers.

14. The lamp apparatus of claim 11, when in the second mode of operation for curing the dental restorative material, the filtered light has a wavelength from 400 to 500 nanometers.

15. The lamp apparatus of claim 12 where the power levels include
    (a) a normal power level where the power density of the light emanating from the tip is substantially constant,
    (b) a ramp power level where the power density of the light emanating from the tip changes in a predetermined fashion,
    (c) a boost power level where the light emanating from the tip is from 15% to 25% greater than at the power density at the normal power level.

16. The lamp apparatus of claim 15 when at the normal power level the power density is from 800 to 1500 milliwatts per square centimeter.

17. The lamp apparatus of claim 15 when at the ramp power level there are a plurality of different patterns of power density which are selectable by the user.

18. The lamp apparatus of claim 1 where the tip has an outlet of a diameter of from 0.1 to 20 millimeters through which an essentially constant, non-intermittent, light beam emanates.

19. A lamp apparatus including
    a handpiece having a tip,
    a light bulb positioned within a reflector which focuses light from the bulb at a predetermined point along an optical path,
    a filter along said optical path in advance of said predetermined point through which a predetermined wavelength of light in the visible range passes, and
    a flexible light guide between the handpiece and said predetermined point which transmits the light of said predetermined wavelength to the tip from which said light emanates, said bulb, when energized, emitting light of sufficient intensity so that the light emanating from the tip has a power density of at least 800 milliwatts per square centimeter, a detector which monitors voltage applied to the bulb and a microprocessor electrically coupled to the detector and responsive thereto to adjust the voltage to maintain the desired power density of light emanating from said tip.

20. The lamp apparatus of claim 1 having a housing enclosing the bulb and the reflector and an AC fan within the housing adjacent to the bulb and reflector fan within the housing adjacent to the bulb and reflector, and a DC fan within the housing adjacent the bulb and reflector, either fan being operated to circulate air through the housing.

21. The lamp apparatus of claim 20 where there is a sensor which detects temperature within said housing and said fan is operated when the temperature exceeds a predetermined limit and an interlock switch that indicates if a panel of the lamp his been disconnected.

22. A lamp apparatus including
a handpiece having a tip,
a light bulb positioned within a reflector which focuses light from the bulb at a predetermined point along an optical path,
a filter along said optical path in advance of said predetermined point through which a predetermined wavelength of light in the visible range passes,
a flexible light guide between the handpiece and said predetermined point which transmits the light of said predetermined wavelength of the tip from which said light emanates,
said bulb, when energized, emitting light of sufficient intensity so that the light emanating from the tip has a power density of at least 800 milliwatts per square centimeter,
a housing to which is selectively attached a control panel at one or the other of two predetermined different locations on the housing.

23. The lamp apparatus of claim 22 where the control panel includes a slave microprocessor and the housing includes a master microprocessor, with said housing having a first cable for connecting the slave and master microprocessors together when the control panel is in the one location and a second cable for connecting the slave and master microprocessors together when the control panel is in the other location, thereby enabling the lamp apparatus to be disposed in different orientations.

24. The lamp apparatus of claim 1 wherein the light guide comprises a liquid enclosed in a flexible tubular member having an inside diameter ranging from 2 to 14 millimeters and a length from 4 to 10 feet, said tubular member being made from a material which is impermeable to the liquid and has a higher refractive index than the liquid.

25. The lamp apparatus of claim 24 wherein the liquid used to transmit the light in the light guide does not wet an internal surface of the light guide that it contacts, is not hygroscopic, transmits in excess of 70% of the light to a handpiece, and has a refractive index lower than that of the material from which the tubular member is made.

26. A lamp apparatus including
a handpiece having a tip,
a light bulb positioned within a reflector which focuses light from the bulb at a predetermined point along an optical path,
a filter along said optical path in advance of said predetermined point through which a predetermined wavelength of light in the visible range passes, and
flexible light guide between the handpiece and said predetermined point which transmits the light of said predetermined wavelength to the tip from which said light emanates,
said bulb, when energized, emitting light of sufficient intensity so that the light emanating from the tip has a power density of at least 800 milliwatts per square centimeter,
a radiometer for reading the power density of the light emanating from the tip.

27. A lamp apparatus including:
a handpiece having a tip,
a light bulb positioned within a reflector which focuses light from the bulb at a predetermined point along an optical path,
a filter along said optical path in advance of said predetermined point through which a predetermined wavelength of light, in the visible range passes, and
a flexible light guide between the handpiece and said predetermined point which transmits the light of said predetermined wavelength to the tip from which said light emanates,
said bulb, when energized, emitting light of sufficient intensity so that the light emanating from the tip has a power density of at least 800 milliwatts per square centimeter,
a display for error messages and a microprocessor programmed to include a routine for handing errors and providing messages for said display.

28. The lamp apparatus of claim 1 including a signal device which alerts a user of the time elapsed while performing certain dental operations.

29. The lamp apparatus of claim 1 including a light sensor which detects light propagating along the optical path and provides a control signal used to regulate voltage being applied to the bulb to maintain the power density of the bulb essentially constant.

30. The lamp apparatus of claim 27 wherein the display for error messages are selected from the group consisting of failure of a bulb, fault in power supply, thermistor errors, solenoid failure, microprocessor memory failure, failure to pass processor self test, radiometer failure, and serial communication port failure.

31. A lamp apparatus including
a handpiece having a tip,
a visible light source comprising a xenon-halogen bulb positioned within an ellipsoidal, dichroic reflector which reflects visible light and focuses said reflected light along an optical path,
a light guide connected to the handpiece which transmits the focused light to said tip, and
a plurality of filters which are selectively moved into the optical path to vary the wavelength of light being transmitted to the tip of the handpiece,
one filter providing light of a first predetermined wavelength that cures light activated dental material, and
another filter providing light of a second predetermined wavelength that bleaches teeth.

32. A lamp apparatus including
an optical system having a bulb which emits light of a high power density, said power density remaining essentially constant at a preset level over the useful life of the bulb, said light being focused at a predetermined position along an optical path and filtered to provide light having a spectrum in the visible range, a bleaching mode where said filtered light has a wavelength particularly suited for bleaching teeth, a curing mode where said filtered light has a wavelength particularly suited to activate light activated restorative dental material, and a flexible light transmitting member which collects the focused visible light and transmits this collected light to an outlet in said member having a diameter of from 2 to 14 millimeters.

33. The lamp apparatus of claim 32 including a source which applies voltage to the bulb, a detector which samples the light from the bulb and provides a control signal, and a microprocessor which is electrically coupled to the detector and in response to the control signal adjusts the voltage applied to the bulb so that the preset level of the light energy may be adjusted.

34. The lamp apparatus of claim 32 where in each of mode of operation there are a plurality of power levels which include (a) a normal power level where the power density of the light emanating from the tip is essentially constant, (b) a ramp power level where the power density of the light emanating from the tip changes in a predetermined fashion, (c) a boost power level where the light emanating from the tip is from 15% to 25% greater than at the power density at the normal power level.

35. The lamp apparatus of claim 32 including a manually operated switch for selectively activating the light source by a user, and a signal device which provides a timing signal that may be detected by the user so that the user will know the duration the light source is activated.

36. A lamp apparatus including a handpiece having a tip, a housing enclosing a visible light source, focusing optics including a flexible light guide connected to the handpiece which transmits focused light from said light source to said tip from which said light emanates, a detachable control panel on the housing which may be detached and attached to different locations, a master microprocessor within the housing for controlling the operations of the lamp apparatus, and a slave microprocessor within the control panel that is connected to the master microprocessor.

37. The lamp apparatus of claim 36 including a detector which detects when the control panel has been detached and provides a control signal, and a control circuit responsive to the control signal which deenergizes the light source to discontinue light emission whenever the control panel is detach and the light source is energized.

38. The lamp apparatus of claim 34 where the control panel is adapted to be attached to different locations on the housing, thereby enabling the lamp apparatus to be disposed in different orientations.

39. The lamp apparatus of claim 36 where the housing has a connector which enables the housing to be attached to a vertical structure.

40. A lamp apparatus including a handpiece through which light is transmitted to a tip of the handpiece, a xenon-halogen bulb positioned within an ellipsoidal, dichroic reflector which focuses the light at a predetermined point along an optical path, a plurality of filters along said optical path in advance of said predetermined point, each different filter passing a different spectrum of visible light, said filters selectively moved into the optical path to vary the wavelength of light being transmitted to the tip of the handpiece to selectively provide a first mode of operation for bleaching of teeth and a second mode of operation for caring of light activated dental restrictive material, a flexible, liquid light guide between the handpiece and said predetermined point which transmits said light from the filters to said tip from which said light emanates, said bulb, when energized, providing light of sufficient power density so that the light emanating from the tip has a power density from 1000 to 2000 milliwatts per square centimeter.

41. The lamp apparatus of claim 40 including a housing in which the bulb and reflector are located, said housing having a wall with an opening therein at which said light is focused, said light guide being mounted on the exterior of the housing, having one end detachably connected to the opening, a detector which detects when the light guide has been detached and provides a control signal, and a control circuit responsive to the control signal which prevents the bulb, from being energized or, if energized, deenergizes the bulb to discontinue light emission.

42. A lamp apparatus including a handpiece having a tip, a light bulb positioned within a reflector which focuses light from the bulb at a predetermined point along an optical path, and a flexible light guide between the handpiece and said predetermined point which transmits the light of said predetermined wavelength to the tip from which said light emanates, and a radiometer having a first operational mode for reading the power density of the light emanating from the tip, and a second operational mode for calibrating the bulb.

43. The lamp apparatus of claim 42 where the bulb has an enclosure holding a mixture of xenon and halogen gases and at a predetermined applied voltage emanates light having a power of 250 watts or greater, said bulb, when energized, emitting light of sufficient intensity so that the light emanating from the tip has a power density of at least 800 milliwatts per square centimeter.

44. The lamp apparatus of claim 43 where the applied voltage is 24 volts.

45. The lamp apparatus of claim 44 where the power density of the light emanating from the tip is from 800 to 2000 milliwatts per square centimeter.

46. A reconfigurable lamp apparatus for use in dental operatory including:

a handpiece having a tip;

a light bulb positioned within a reflector which focuses light from the bulb at a predetermined point along an optical path;

a flexible light guide connected to the handpiece that transmits light from the bulb to the tip;

a box-like housing having a top, a bottom, a front and a rear;

a control panel that is either attached to the top of the housing by a user when the lamp apparatus is configured into a horizontal position or is attached to the rear of the housing by a user when the lamp apparatus is configured into a vertical position; and an interlock switch mounted to the housing and positioned to detect when the control panel is attached to the top or attached to the rear of the lamp apparatus.

47. The lamp apparatus of claim 41 which weighs less than 15 pounds.

* * * * *